United States Patent
Lin et al.

(10) Patent No.: US 8,012,210 B2
(45) Date of Patent: Sep. 6, 2011

(54) IMPLANT FRAMES FOR USE WITH SETTABLE MATERIALS AND RELATED METHODS OF USE

(75) Inventors: Jo-Wen Lin, Philadephia, PA (US); Erik O. Martz, Savage, MN (US); Joel F. Millets, Bradley Beach, NJ (US); Daniel Rosenthal, Short Hills, NJ (US); David Chow, West Chester, PA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 669 days.

(21) Appl. No.: 11/032,891

(22) Filed: Jan. 11, 2005

(65) Prior Publication Data

US 2005/0209696 A1    Sep. 22, 2005

Related U.S. Application Data

(60) Provisional application No. 60/537,067, filed on Jan. 16, 2004.

(51) Int. Cl.
 *A61F 2/44* (2006.01)
(52) U.S. Cl. ........ 623/17.12; 623/17.11; 623/17.16
(58) Field of Classification Search .... 623/17.11–17.16; *A61F 2/44*
 See application file for complete search history.

(56) References Cited

U.S. PATENT DOCUMENTS

| | | |
|---|---|---|
| 3,892,649 A | 7/1975 | Phillips et al. |
| 3,919,773 A | 11/1975 | Freeman |
| 3,949,073 A | 4/1976 | Daniels et al. |
| 4,183,874 A | 1/1980 | Fan et al. |
| 4,551,156 A | 11/1985 | Li |
| 4,595,713 A | 6/1986 | St. John |
| 4,637,931 A | 1/1987 | Schmitz |
| 4,638,045 A | 1/1987 | Kohn et al. |
| 4,645,503 A | 2/1987 | Lin et al. |
| 4,655,777 A | 4/1987 | Dunn et al. |
| 4,743,259 A | 5/1988 | Bolander et al. |
| 4,783,504 A | 11/1988 | St. Clair et al. |
| 4,806,621 A | 2/1989 | Kohn et al. |
| 4,880,610 A | 11/1989 | Constantz |
| 4,882,149 A | 11/1989 | Spector |
| RE33,161 E | 2/1990 | Brown et al. |
| 4,902,296 A | 2/1990 | Bolander et al. |

(Continued)

FOREIGN PATENT DOCUMENTS

EP    0 413 492    2/1991

(Continued)

OTHER PUBLICATIONS

Allcock et al., "Hydrolysis pathways for aminophosphazenes", *Inorg. Chem.*, 21:515-21, 1982.

(Continued)

*Primary Examiner* — David Isabella
*Assistant Examiner* — Jason-Dennis Stewart

(57) ABSTRACT

Intervertebral implant system for intervertebral implantation, are disclosed. An intervertebral implant system according to the present disclosure includes a frame having a peripheral wall defining a space therein, and a settable material introducible into the space of the frame. The settable material is a biocompatible load bearing material including and not limited to bone, composites, polymers of bone growth material, collagen, and insoluble collagen derivatives. The settable material is injectable into the space defined by the frame. The settable material may have an initial fluid condition wherein the fluid settable material cures to a hardened condition.

21 Claims, 27 Drawing Sheets

U.S. PATENT DOCUMENTS

| | | | |
|---|---|---|---|
| RE33,221 E | 5/1990 | Brown et al. | |
| 4,946,929 A | 8/1990 | d'Amore et al. | |
| 5,010,167 A | 4/1991 | Ron et al. | |
| 5,019,379 A | 5/1991 | Domb et al. | |
| 5,034,059 A | 7/1991 | Constantz | |
| 5,047,031 A | 9/1991 | Constantz | |
| 5,053,212 A | 10/1991 | Constantz | |
| 5,129,905 A | 7/1992 | Constantz | |
| 5,146,933 A * | 9/1992 | Boyd | 128/899 |
| 5,149,368 A | 9/1992 | Liu et al. | |
| 5,162,445 A | 11/1992 | Powers et al. | |
| 5,246,782 A | 9/1993 | Kennedy et al. | |
| 5,262,166 A | 11/1993 | Liu et al. | |
| 5,262,461 A | 11/1993 | Serizawa et al. | |
| 5,290,555 A | 3/1994 | Guthauser et al. | |
| 5,290,558 A | 3/1994 | O'Leary et al. | |
| 5,324,519 A | 6/1994 | Dunn et al. | |
| 5,333,626 A | 8/1994 | Morse et al. | |
| 5,336,264 A | 8/1994 | Constanz | |
| 5,352,715 A | 10/1994 | Wallace et al. | |
| 5,399,665 A | 3/1995 | Barrera et al. | |
| 5,417,975 A | 5/1995 | Lussi et al. | |
| 5,462,722 A | 10/1995 | Liu et al. | |
| 5,468,544 A | 11/1995 | Marcolongo et al. | |
| 5,507,813 A | 4/1996 | Dowd et al. | |
| 5,512,600 A | 4/1996 | Mikos et al. | |
| 5,513,662 A | 5/1996 | Morse et al. | |
| 5,514,378 A | 5/1996 | Mikos et al. | |
| 5,525,148 A | 6/1996 | Chow et al. | |
| 5,542,973 A | 8/1996 | Chow et al. | |
| 5,552,454 A | 9/1996 | Kretschmann et al. | |
| 5,573,771 A | 11/1996 | Geistlich et al. | |
| 5,605,713 A | 2/1997 | Boltong | |
| 5,606,000 A | 2/1997 | Jadhav et al. | |
| 5,624,463 A | 4/1997 | Stone et al. | |
| 5,626,861 A | 5/1997 | Laurencin et al. | |
| 5,641,502 A | 6/1997 | Skalla et al. | |
| 5,650,176 A | 7/1997 | Lee et al. | |
| 5,679,723 A | 10/1997 | Cooper et al. | |
| 5,696,175 A | 12/1997 | Mikos et al. | |
| 5,716,404 A | 2/1998 | Vacanti et al. | |
| 5,716,413 A | 2/1998 | Walter et al. | |
| 5,717,006 A | 2/1998 | Daculsi et al. | |
| 5,736,372 A | 4/1998 | Vacanti et al. | |
| 5,766,618 A | 6/1998 | Laurencin et al. | |
| 5,766,637 A | 6/1998 | Shine et al. | |
| 5,770,417 A | 6/1998 | Vacanti et al. | |
| 5,804,178 A | 9/1998 | Vacanti et al. | |
| 5,817,328 A | 10/1998 | Gresser et al. | |
| 5,837,752 A | 11/1998 | Shastri et al. | |
| 5,846,484 A | 12/1998 | Scarborough et al. | |
| 5,846,951 A | 12/1998 | Gregoriadis | |
| 5,863,297 A | 1/1999 | Walter et al. | |
| 5,899,939 A | 5/1999 | Boyce et al. | |
| 5,902,599 A | 5/1999 | Anseth et al. | |
| 5,948,386 A | 9/1999 | Katti et al. | |
| 5,977,204 A | 11/1999 | Boyan et al. | |
| 6,001,394 A | 12/1999 | Daculsi et al. | |
| 6,002,065 A | 12/1999 | Constantz et al. | |
| 6,027,744 A | 2/2000 | Vacanti et al. | |
| 6,030,635 A | 2/2000 | Gertzman et al. | |
| 6,033,852 A | 3/2000 | Andle et al. | |
| 6,095,148 A | 8/2000 | Shastri et al. | |
| 6,117,456 A | 9/2000 | Lee et al. | |
| 6,119,028 A | 9/2000 | Schulman et al. | |
| 6,123,727 A | 9/2000 | Vacanti et al. | |
| 6,123,731 A | 9/2000 | Boyce et al. | |
| 6,127,442 A | 10/2000 | Sulzbach et al. | |
| 6,132,468 A | 10/2000 | Mansmann | |
| 6,156,068 A | 12/2000 | Walter et al. | |
| 6,165,486 A | 12/2000 | Marra et al. | |
| 6,180,606 B1 | 1/2001 | Chen et al. | |
| 6,183,498 B1 | 2/2001 | Devore et al. | |
| 6,187,048 B1 * | 2/2001 | Milner et al. | 623/17.12 |
| 6,203,573 B1 | 3/2001 | Walter et al. | |
| 6,206,957 B1 | 3/2001 | Driessens et al. | |
| 6,224,630 B1 | 5/2001 | Bao et al. | |
| 6,261,586 B1 * | 7/2001 | McKay | 424/423 |
| 6,294,041 B1 | 9/2001 | Boyce et al. | |
| 6,294,187 B1 | 9/2001 | Boyce et al. | |
| 6,328,990 B1 | 12/2001 | Ducheyne et al. | |
| 6,332,779 B1 | 12/2001 | Boyce et al. | |
| 6,340,477 B1 | 1/2002 | Anderson | |
| 6,352,667 B1 | 3/2002 | English | |
| 6,376,573 B1 | 4/2002 | White et al. | |
| 6,399,693 B1 | 6/2002 | Brennan et al. | |
| 6,406,498 B1 | 6/2002 | Törmälä et al. | |
| 6,432,436 B1 | 8/2002 | Gertzman et al. | |
| 6,437,018 B1 | 8/2002 | Gertzman et al. | |
| 6,440,444 B2 | 8/2002 | Boyce et al. | |
| 6,441,073 B1 | 8/2002 | Tanaka et al. | |
| 6,471,993 B1 | 10/2002 | Shastri et al. | |
| 6,478,825 B1 | 11/2002 | Winterbottom et al. | |
| 6,511,511 B1 | 1/2003 | Slivka et al. | |
| 6,558,424 B2 * | 5/2003 | Thalgott | 623/17.16 |
| 6,605,089 B1 * | 8/2003 | Michelson | 606/61 |
| 6,616,698 B2 | 9/2003 | Scarborough | |
| 6,620,196 B1 * | 9/2003 | Trieu | 623/17.16 |
| 6,648,917 B2 * | 11/2003 | Gerbec et al. | 623/17.11 |
| 6,696,073 B2 | 2/2004 | Boyce et al. | |
| RE38,522 E | 5/2004 | Gertzman et al. | |
| 6,808,585 B2 | 10/2004 | Boyce et al. | |
| 6,835,206 B2 * | 12/2004 | Jackson | 623/17.11 |
| 6,846,328 B2 * | 1/2005 | Cauthen | 623/17.11 |
| 6,867,240 B2 | 3/2005 | Ma et al. | |
| 6,890,355 B2 * | 5/2005 | Michelson | 623/17.11 |
| 6,911,212 B2 | 6/2005 | Gertzman et al. | |
| 6,933,328 B2 | 8/2005 | Schacht | |
| 6,936,070 B1 * | 8/2005 | Muhanna | 623/17.12 |
| 6,969,404 B2 * | 11/2005 | Ferree | 623/17.11 |
| 6,984,246 B2 * | 1/2006 | Huang | 623/17.13 |
| 7,004,974 B1 | 2/2006 | Larsson et al. | |
| 7,033,393 B2 * | 4/2006 | Gainor et al. | 623/17.11 |
| 7,122,057 B2 | 10/2006 | Beam et al. | |
| 7,156,880 B2 | 1/2007 | Evans et al. | |
| 7,166,133 B2 | 1/2007 | Evans et al. | |
| 7,179,299 B2 | 2/2007 | Edwards et al. | |
| 7,186,759 B2 | 3/2007 | Seppala et al. | |
| 7,235,107 B2 | 6/2007 | Evans et al. | |
| 7,241,316 B2 | 7/2007 | Evans et al. | |
| 7,270,813 B2 | 9/2007 | Shimp et al. | |
| 7,276,081 B1 * | 10/2007 | Coates et al. | 623/17.11 |
| 7,291,345 B2 | 11/2007 | Winterbottom et al. | |
| 7,361,369 B2 | 4/2008 | Liebschner | |
| 7,547,449 B2 | 6/2009 | Gower et al. | |
| 2001/0051833 A1 | 12/2001 | Walter et al. | |
| 2002/0055782 A1 * | 5/2002 | Bagby | 623/17.16 |
| 2002/0098222 A1 | 7/2002 | Wironen et al. | |
| 2002/0116064 A1 * | 8/2002 | Middleton | 623/17.16 |
| 2002/0161443 A1 * | 10/2002 | Michelson | 623/17.11 |
| 2003/0045942 A1 | 3/2003 | Lai et al. | |
| 2003/0114936 A1 | 6/2003 | Sherwood et al. | |
| 2003/0180344 A1 | 9/2003 | Wise et al. | |
| 2003/0199984 A1 * | 10/2003 | Trieu | 623/17.16 |
| 2004/0024457 A1 | 2/2004 | Boyce et al. | |
| 2004/0059417 A1 * | 3/2004 | Smith et al. | 623/17.11 |
| 2004/0078085 A1 * | 4/2004 | Pointillart et al. | 623/23.51 |
| 2004/0137032 A1 | 7/2004 | Wang | |
| 2004/0138758 A1 | 7/2004 | Evans et al. | |
| 2004/0146543 A1 | 7/2004 | Shimp et al. | |
| 2004/0167625 A1 * | 8/2004 | Beyar et al. | 623/11.11 |
| 2004/0197373 A1 | 10/2004 | Gertzman et al. | |
| 2004/0228898 A1 | 11/2004 | Ross et al. | |
| 2004/0236425 A1 * | 11/2004 | Huang | 623/17.12 |
| 2004/0249462 A1 * | 12/2004 | Huang | 623/17.13 |
| 2004/0253290 A1 | 12/2004 | Kim et al. | |
| 2005/0013793 A1 | 1/2005 | Beckamn et al. | |
| 2005/0027033 A1 | 2/2005 | Knaack et al. | |
| 2005/0042253 A1 | 2/2005 | Farrar et al. | |
| 2005/0049705 A1 * | 3/2005 | Hale et al. | 623/17.11 |
| 2005/0065607 A1 * | 3/2005 | Gross | 623/17.11 |
| 2005/0070900 A1 * | 3/2005 | Serhan et al. | 606/61 |
| 2005/0080486 A1 * | 4/2005 | Fallin et al. | 623/17.11 |
| 2005/0100578 A1 | 5/2005 | Schmid et al. | |
| 2005/0238683 A1 | 10/2005 | Adhikari et al. | |
| 2005/0249773 A1 | 11/2005 | Maspero et al. | |
| 2005/0251266 A1 | 11/2005 | Maspero et al. | |

| | | | |
|---|---|---|---|
| 2005/0251267 A1 | 11/2005 | Winterbottom et al. | |
| 2005/0281856 A1 | 12/2005 | McGlohorn et al. | |
| 2006/0067971 A1 | 3/2006 | Story et al. | |
| 2006/0067973 A1 | 3/2006 | Schachter | |
| 2006/0127442 A1 | 6/2006 | Helmus | |
| 2006/0216323 A1 | 9/2006 | Knaack et al. | |
| 2006/0263335 A1 | 11/2006 | France et al. | |

FOREIGN PATENT DOCUMENTS

| | | |
|---|---|---|
| WO | WO-91/09079 | 6/1991 |
| WO | WO-98/19718 | 5/1998 |
| WO | WO-2004/032988 | 4/2004 |
| WO | WO-2004/053112 | 6/2004 |
| WO | WO-2005/107651 | 11/2005 |
| WO | WO-2007/084725 | 7/2007 |

OTHER PUBLICATIONS

Allcock et al., "Synthesis of poly (amino acid alkyl ester) phosphazenes", *Macromolecules*, 10:824-30,. 1977.

Baker, Gregory L., http://www.cem.msu.edu/~gradoff/brochf/Baker.htm, printed Aug. 2002.

Boesch, P., "Bone Grafting with Fibrin Glue", *Wiener Klinische Wochenschroft Supplementum*, 93, No. 124, pp. 3-26, 1981.

Bohner et al., "Injectability of calcium phosphate pastes", *Biomaterials*, 26:1553-63, 2005.

Bohner et al., "Theoretical and experimental model to describe the injection of a polymethylmethacrylate cement into a porous structure", *Biomaterials*, 24:2721-30, 2003.

de Wijn et al., "Grafting PMMA on Hydroxyapatite Powder Particles using Isocyanatoethylmethacrylate", Fifth World Biomaterials Congress, May 29-Jun. 2, 1996, Toronto, CA.

Eggli et al., "Porous Hydroxyapatite and tricalcium phosphate cylinders with two different pore size ranges implanted in the cancellous bone of rabbits", *Clin Orthop.*, 232:127-38, 1987.

Forssell et al., "Experimental Osteosynthesis with Liquid Ethyl Cyanacrylate Polymerized with Ultrasound", *Arch. Orthop Trauma Surg*, 103:278-83, 1984.

Giannitsios et al.,"High Cement Viscosity Reduces Leakage Risk in Vertebroplasty", European Cells and Materials, 10(3):54, 2005.

Han, et al., "Synergistic Effects of Lecithin and Human DBM on Bone Induction in Nude Rats", *Society for Biomaterials*, 28th Annual Meeting Transactions, 2002 (abstract).

Hooper, et al., "Diphenolic Monomers Derived from the Natural Amino Acid α-L-Tyrosine: An Evaluation of Peptide Coupling Techniques", *Journal of Bioactive and Compatible Polymers* 10, 327-340 (1995).

Hurley et al., "Anorganic Bone—Chemistry, Anatomy, and Biological Reactions"*Milit. Med.*, 101-4, 1957.

International Search Report for PCT/US03/25417, date of mailing Jul. 2, 2004.

International Search Report for PCT/US03/39704, date of mailing Jun. 2, 2004.

International Search Report, PCT/US05/15426, date of mailing Jun. 15, 2006.

International Search Report, PCT/US07/001540, date of mailing Oct. 2, 2007.

James et al., "Small changes in polymer chemistry have a large effect on the bone-implant interface: evaluation of a series of degradable tyrosine-derived polycarbonates in bone defects", *Biomaterials*, 20: 2203-313, 1999.

Karageorgiou et al., "Porosity of 3D biomaterial scaffolds and osteogenesis", *Biomaterials*, 26: 5474-91, 2005.

Kershaw, "Preparation of Anorganic Bone Grafting Material", *Pharm. J.*, 6: 537, 1963.

Klaitwatter et al., "Application of porous ceramics for the attachment of load bering orthopedic applications", *J. Biomed. Mater. Res. Symp.*, 2: 161, 1971.

Langer, "Biomaterials in drug delivery and tissue engineering: one laboratory's experience", *Acc. Chem. Res.*, 33: 94, 2000.

Langer, "Selected advances in drug delivery and tissue engineering", *J. Control Release*, 62: 7, 1999.

Lewandrowski et al., "Kinetics of cortical bone demineralization: Controlled demineralization-a new method for modifying cortical bone allografts", *J. Biomed. Mater. Res.*, 31: 365-72, 1996.

Liu et al., "Covalent Bonding of PMMA, PBMA, and ply(HEMA) to Hydroxyapatite Particles", *J. Biomed. Mater. Res.*, 40: 257-63, 1998.

Mikos et al., "Prevascularization of biodegradable polymer scaffolds for hepatocyte transplantation", *Proc. ACS Div. of Polymer Mater.*, 66: 33, 1992.

Murphy et al., "Salt Fusion: An Approach to Improve Pore Interconeectivity withing Tissue Engineering Scaffolds", *Tissue Engineering*, 8(1): 43-52, 2002.

Nazhat, S.N., et al., "Dynamic Mechanical Behaviour of Modified Hydroxyapatite Reinforced Polyethylene Composites", *Fifth World Biomaterials Congress*, p. 83, May 29-Jun. 2 (1996).

Reddi et al., "Biochemical Sequences in the Transformation of Normal Fibroblasts in Adolescent Rats", *Proc. Natl. Acad. Sci. USA*, 69:1601-1605, 1972.

Satish Pulapura, et al., "Tyrosine-Derived Polycarbonates: Backbone-Modified "Pseudo"-Poly (Amino Acids) Designed for Biomedical Applications", *Biopolymers* 32, 411-417 (1992).

Schmitz et al., "A Preliminary Study of the Osteogenic Potential of a Biodegradable Alloplastic-Osteoinductive Alloimplant", *Clinical Orthopaedics and Related Research*, 237: 245-55, 1988.

"Silane Coupling Agent", http://www.apr.co.kr/silaneen.htm, printed Aug. 7, 2002.

Simmons et al., "Evaluation of collagen cross-linking techniques for the stabilization of tissue matrices", *Biotechnol. Appl. Biochem.*, 17: 23-9, 1993.

Tangpasuthadol, Varawut, "Thermo-Mechanical Properties and Hydrolytic Degradation of Tyrosine-Derived Polymers for Use in Biomedical Applications", Ph.D. Dissertation, Rutgers, The State University of New Jersey, (Jan. 1999).

Uhrich et al., "Polymeric systems for controlled drug release", *Chem. Rev.*, 99: 3181, 1999.

Vogt et al., "Fabrication of Highly Porous Scaffold Materials based on Functionalized Oligolactides and Preliminary Results on Their Use in Bone Tissue Engineering", *European Cells and Materials*, 4: 30-38, 2002.

White et al., "Biomaterial aspects of Interpore 200 porous hydroxyapatite", *Dental Cliical of N. Amer.*, 30: 49-67, 1986.

Whittaker, et al., "Matrix Metalloproteinases and their Inhibitors—Current Status and Future Challenges", *Celltransmissions*, 17, prior to Jun. 13, 2002.

Written Opinion, PCT/US07/001540, date of mailing Oct. 2, 2007.

Zhiyuan Zhong, et al., "Calcium methoxide initiated ring-opening polymerization of ϵ-caprolactone and L-lactide", *Polymer Bulletin* 46, 51-57 (2001).

* cited by examiner

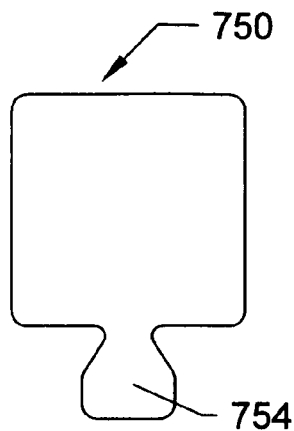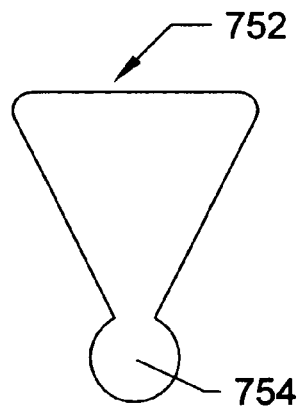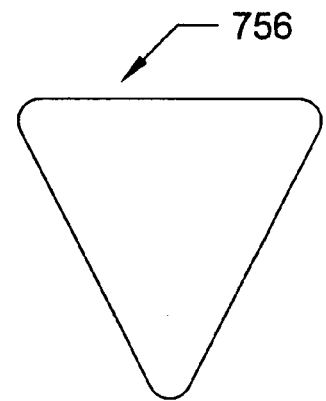
Figure 87　　　Figure 88　　　Figure 89
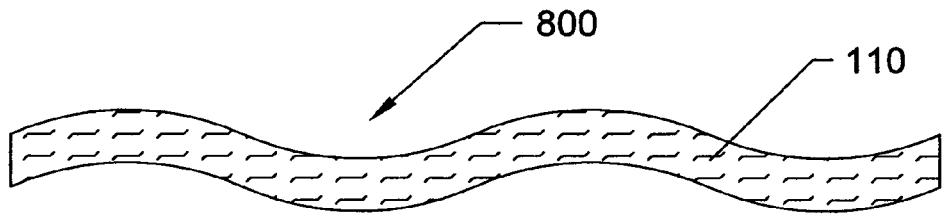
Figure 90
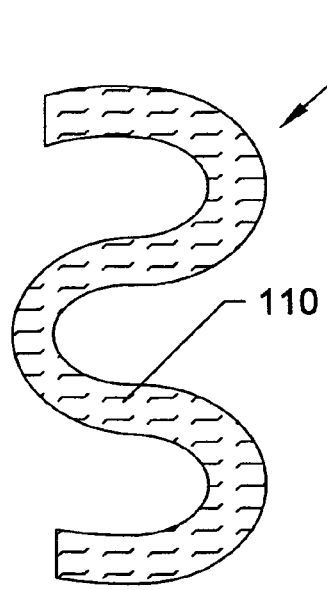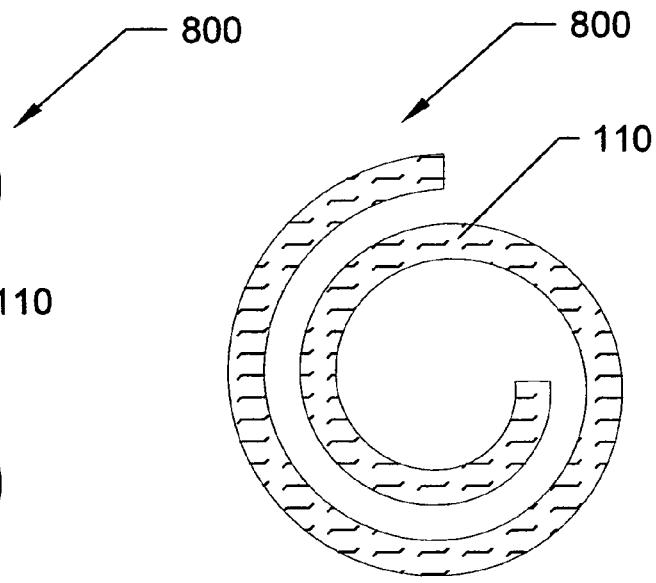
Figure 91　　　　　　Figure 92

IMPLANT FRAMES FOR USE WITH SETTABLE MATERIALS AND RELATED METHODS OF USE

CROSS-REFERENCE TO RELATED APPLICATION

The present application claims the benefit of and priority to U.S. Provisional Application No. 60/537,067, filed on Jan. 16, 2004, the entire disclosure of which is incorporated herein by reference.

BACKGROUND

1. Technical Field

The present disclosure relates to intervertebral implants and, more particularly to ribbon or band-like frames for implantation into the spine to promote inter-body spinal fusion. The present disclosure also relates to methods of using the same.

2. Background of Related Art

The spine is a flexible column formed of a series of bone called vertebrae. The vertebrae are hollow and piled one upon the other with a disc disposed between each one, forming a strong hollow column for support of the cranium and trunk. The hollow core of the spine houses and protects the nerves of the spinal cord. The vertebrae are connected together by means of articular processes and intervertebral, fibro-cartilagineous spaces.

The intervertebral fibro-cartilages are also known as intervertebral disks and are made of a fibrous ring filled with pulpy material. The disks function as spinal shock absorbers and also cooperate with synovial joints to facilitate movement and maintain flexibility of the spine. When one or more disks rupture or degenerate through accident or disease, nerves passing near the affected area may be compressed and are consequently irritated. The result may be chronic and/or debilitating back pain. Various methods and apparatus, both surgical and non-surgical, have been designed to relieve such back pain.

One such method of treating back pain in patients with ruptured or degenerated intervertebral discs (e.g., spondylolisthesis or other pathologies) involves the fusing of adjacent vertebrae to on another. Typically during such a procedure, a spinal implant, having a shape approximating the shape of the space between the adjacent vertebrae (i.e., the intervertebral space), is placed into the intervertebral space in a position to engage the adjoining vertebrae. The implant is constructed from a biocompatible material which is adapted to fuse with the adjacent vertebrae to thereby maintain proper spacing and lordosis between the adjacent vertebrae.

While use of spinal implants is known, a continuing need exists for improvements in spinal implants which provide an improved biomechanical construct when implanted, is better able to conform to the end plates of the vertebrae, and is better able to distribute the load across the end plates and reduce regions of pressure concentration.

SUMMARY

Intervertebral implant systems for intervertebral implantation, are disclosed. According to an aspect of the present disclosure, an intervertebral implant system includes a frame having a peripheral wall defining a space therein, and a settable material introducible into the space of the frame.

The frame may be constructed from at least one of titanium, titanium alloy, steel, shape memory alloy, resorbable polymer, non-resorbable polymer, ceramic, and organic materials. The settable material is desirably a biocompatible load bearing material. In one embodiment, the settable material may include bone, composites, polymers of bone growth material, collagen, and insoluble collagen derivatives.

Desirably, the settable material is injectable into the space defined by the frame. The settable material has an initial fluid condition and is curable to a hardened condition.

In one embodiment, at least one of an upper edge and a lower edge of the frame are shaped. It is envisioned that at least one of the upper edge of the frame and the lower edge of the frame includes a plurality of projections formed along a length of the frame and/or a continuous projection extending along a length of the frame.

Desirably, the frame is flexible along at least a portion of a length thereof. The frame may include a pair of free ends. The free ends of the frame may be joined to one another.

In one embodiment, the intervertebral implant system includes a cap which is positionable within the space defined by the frame. The cap is dimensioned to extend beyond at least each free end of the frame. In an embodiment, the frame is linearly expandable.

It is envisioned that the frame may include at least one opening formed in the peripheral wall. The intervertebral implant system further includes at least one plug configured and dimensioned for insertion into each opening of the frame. The at least one plug prevents the escape of the settable material from the space defined by the frame.

The peripheral wall of the frame is at least partially collapsible. The frame may be substantially wedge-shaped. It is envisioned that the peripheral wall includes at least one of a planar inner surface and a planar outer surface. In certain embodiments, the peripheral wall includes at least one of a convex inner surface and a planar outer surface. In other embodiments, the peripheral wall includes at least one of a concave inner surface and a planar outer surface. In some embodiments, the peripheral wall may include at least one of a saw-toothed inner and outer surface.

In an embodiment, the peripheral wall of the frame defines a cylindrical body portion having an aperture formed therein. The frame further includes an upper surface connected to an upper edge of the peripheral wall; a lower surface connected to a lower edge of the peripheral wall; a first stub extending from the upper surface; and a second stub extending from the lower surface.

The frame may include an upper and a lower ring each having a dimension. The first stub may include a first and a second ring each having a dimension smaller than the dimension of the rings of the frame, wherein the first ring of the first stub is in the plane of the upper ring of the frame. The second stub may include a first and a second ring each having a dimension smaller than the dimension of the rings of the frame, wherein the first ring of the second stub is in the plane of the lower ring of the frame. The frame may include a membrane enclosing each of the rings thereof.

Desirably, a length of the perimetral wall defining the space of the frame is adjustable. The peripheral wall desirably has an I-shaped transverse cross-sectional profile.

In one embodiment, the frame is an inflatable balloon. Accordingly, the balloon is inflatable with settable material. Desirably, the balloon has a substantially rectangular and triangular shape. The balloon may be fabricated from a resorbable material.

In one embodiment, it is envisioned that the peripheral wall is fabricated from strands of resorbable polymers.

The intervertebral implant system may include a support plate securable to adjacent intervertebral discs; and a fixation means extendable through the support plate and into the peripheral wall of the frame.

According to another aspect of the present disclosure, a method of performing an intervertebral surgical technique, is provided. The method includes the steps of providing an intervertebral implant system for intervertebral implantation. The intervertebral implant system includes a frame having a peripheral wall defining a space therein, and a settable material introducible into the space of the frame.

The method further includes the steps of accessing the disc space between adjacent intervertebral discs; removing disc material from the disc space; distracting the disc space; preparing the end plates of the adjacent intervertebral discs; inserting the peripheral wall of the frame into the disc space, between the adjacent intervertebral discs; and injecting settable material into the space defines by the peripheral wall of the frame and between the adjacent intervertebral discs.

The method may further include the step of connecting each free end of the peripheral wall to one another. The implant system may include a cap. Accordingly, the method further includes the step of placing the cap across and between each free end of the peripheral wall of the frame following injection of settable material into the space. Desirably, the cap is placed inside the space.

The method further includes the steps of inserting a plurality of frames into the disc space between the adjacent intervertebral discs, wherein each frame defines a space; and injecting settable material into at least one of the spaces defined by the frames.

The method may further include the steps of inserting a first frame into a portion of the disc space between the adjacent intervertebral discs, the first frame defining a first space; inserting a second frame into at least one of a portion of the disc space between the adjacent intervertebral discs and the space defined by the first frame, the second frame defining a second space; and injecting settable material into at least one of the first and second space.

It is envisioned that the frame has an initial constricted condition, and wherein the method further includes the step of expanding the frame to expand the space. The peripheral wall of the frame is manipulated to form frame into at least one of a circular, elliptical, triangular and kidney shape. The peripheral wall of the frame desirably includes an aperture formed therein, wherein the method includes the steps of injecting settable material into the space defined by the frame through the aperture formed in the peripheral wall.

The implant system may further include a plug for occluding the aperture formed in the peripheral wall of the frame.

In one embodiment, the implant system includes a cannulated instrument having a distal end configured and dimensioned for insertion into the disc space, wherein the peripheral wall is introduced into the disc space by the cannulated instrument. Accordingly, the peripheral wall of the frame is introduced into the disc space and the settable material is introduced into the space of the frame through the cannulated instrument.

According to one method, the peripheral wall of the frame is positionable about a distal end of the cannulated instrument. The method may include the steps of positioning the peripheral wall of the frame about the distal end of the cannulated instrument; inserting the distal end of the cannulated instrument into the disc space such that a portion of the peripheral wall is positioned in the disc space; and dispensing settable material from the distal end of the cannulated instrument to expand the frame into the disc space and to fill the space defined by the frame with settable material.

According to an embodiment, the cannulated instrument includes at least one plunger slidably disposed in a lumen of the instrument. Accordingly, the method includes the steps of positioning the peripheral wall of the frame about the distal end of the cannulated instrument; inserting the distal end of the cannulated instrument into the disc space such that a portion of the peripheral wall is positioned in the disc space; extending at least one plunger from the distal end of the cannulated instrument to deploy the peripheral wall of the frame at least partially into the disc space; withdrawing the at least one plunger from the lumen of the cannulated instrument; and dispensing settable material from the lumen of the cannulated instrument to expand the frame into the disc space and to fill the space defined by the frame with settable material.

BRIEF DESCRIPTION OF THE DRAWINGS

Various preferred embodiments are described herein with reference to the drawings wherein:

FIG. 87 is a top plan view of a template for forming a frame for insertion between the vertebral discs;

FIG. 88 is a top plan view of another template for forming a frame for insertion between the vertebral discs;

FIG. 89 is a top plan view of yet another template for forming a frame for insertion between the vertebral discs;

FIG. 90 is a plan view of a frame according to another embodiment of the present disclosure;

FIG. 91 is a plan view of the frame of FIG. 90 in a first configuration; and

FIG. 92 is a plan view of the frame of FIG. 90 in a second configuration.

DETAILED DESCRIPTION OF PREFERRED EMBODIMENTS

Figure 1:
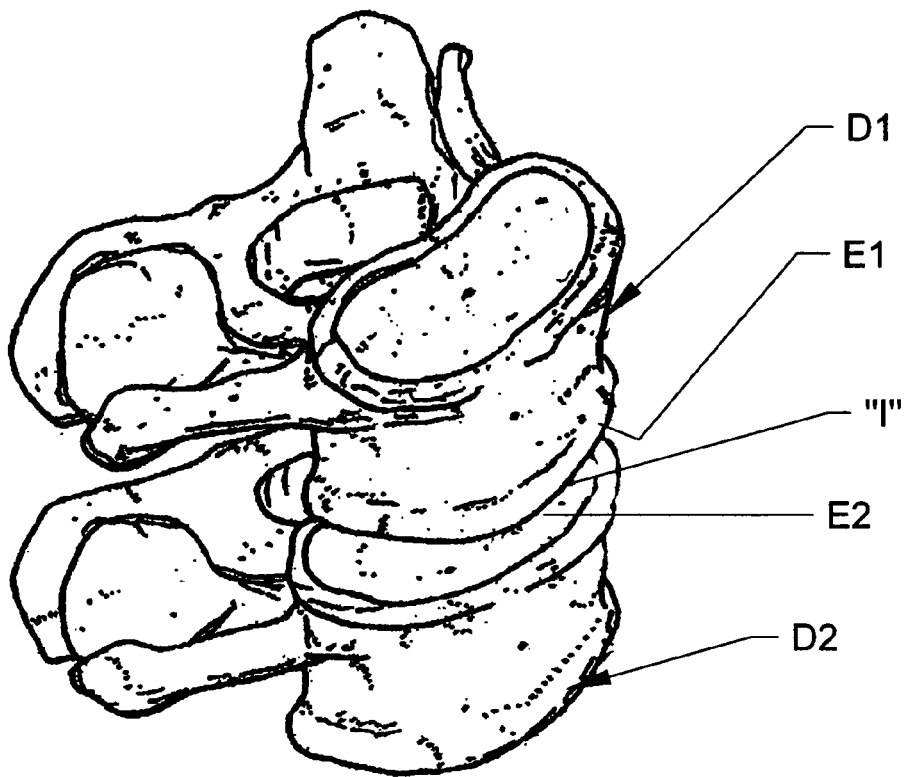
FIG. 1 is a perspective view of a pair of adjacent vertebral discs.

Preferred embodiments of the presently disclosed implant ribbon or band-like frame for use with settable material will now be described in detail with reference to the drawings, in which like reference numerals designate identical or corresponding elements in each of the several views. While the following disclosure will relate primarily to interbody fusion of vertebral bodies, it is envisioned that fusion of any bony motion segment (e.g., ankle, finger, wrist, knee, etc.) falls within the scope and coverage of the present disclosure.

Initially, with reference to FIG. 1, a pair of adjacent vertebral discs is shown generally as $D_1$ and $D_2$. Each vertebral disc $D_1$ and $D_2$ defines an upper end plate $E_1$ and a lower end plate $E_2$.

The term "osteogenic" as utilized herein shall be understood as referring to the ability of an osteoimplant to enhance or accelerate the growth of new bone tissue by one or more mechanisms such as osteogenesis, osteoconduction and/or osteoinduction.

The term "osteoinductive" as utilized herein shall be understood to refer to the ability of a substance to recruit cells from the host that have the potential for forming new bone and repairing bone tissue. Most osteoinductive materials can induce bone formation and stimulate the formation of ectopic bone in soft tissue.

The term "osteoconductive" as utilized herein shall be understood to refer to the ability of a substance to serve as a suitable template or substrate along which bone may grow. Additionally, the term osteoconductive refers to the ability of a material to provide a three-dimensional porous framework, a scaffold or matrix for new bone growth and remodeling which conducts the ingrowth of new living bone into the framework, scaffold or matrix.

The term "osteoimplant" as utilized herein contemplates any device or material for implantation that aids or augments bone or other hard tissue formation or healing for human or animal use. Osteoimplants are often applied at a bone defect or dental repair site, e.g., one resulting from injury, defect brought about during the course of surgery, infection, malignancy or developmental malformation. Osteoimplants are envisioned as being suitably sized and shaped as required for use in a wide variety of orthopedic, neurosurgical, oral and maxillofacial and dental surgical procedures, such as the repair of simple and compound fractures and non-unions, external and internal fixations, joint reconstructions such as arthrodesis, general arthroplasty, deficit filling, discectomy, laminectomy, anterior cervical and thoracic operations, spinal fusions, dental restorations, etc. Therefore, the osteoimplants herein are intended for implantation at a bony site. As used herein, the term "osteoimplant" is to be interpreted in its broadest sense and is not intended to be limited to any particular shape, size, configuration or application.

The term "shaping" refers to any of the various methods that can be used, individually or in combination, to provide an osteoimplant of a desired size and configuration. Such methods are known to those skilled in the art include, for example, machining, laser etching, welding, assembling of parts, cutting, milling, reactive etching, etc. Where the osteoimplant comprises particles or pieces, "shaping" also refers to extruding, injection molding, solvent casting, vacuum forming, sintering, melt forming, reaction molding, compression molding, transfer molding, blow molding, rotational molding, thermoforming, machining, CAD/CAM procedures, and the like. Shaping also includes any post-shaping operations that may be utilized to modify the internal and/or external structure of the osteoimplant and/or modify its properties, e.g., selective removal of a filler component to provide voids, application of a layer of biologically active material to part or all of the surface and/or subsurface region of the osteoimplant, etc.

The term "biocompatible" and expressions of like import shall be understood to mean the absence any undesirable biological response to an implant. Optional components that are useful can be considered biocompatible if, at the time of implantation, they do not elicit a significant undesirable response in vivo.

The term "autograft" as utilized herein refers to grafts made of autogenic bone that is obtained from the intended recipient of the implant.

The term "allograft" as utilized herein refers to grafts, from a donor of the same species, which may be processed to remove cells and/or other components, intended for implantation that is taken from a different member of the same species as the intended recipient. Thus, the term "allograft" includes bone from which substantially all cellular matter has been removed (processed acellular bone) as well as cell-containing bone.

The term "bioresorbable" as utilized herein refers to those materials of either synthetic or natural origin which, when placed in a living body, are degraded through either enzymatic, hydrolytic or other chemical reactions or cellular processes into by-products which are either integrated into, or expelled from, the body. It is recognized that in the literature, the terms "resorbable", "absorbable", "bioresorbable" and "bioabsorbable" are frequently used interchangeably.

In accordance with the present disclosure and as will be described in greater detail below, at least one implant frame 100 is provided for positioning between vertebral discs $D_1$ and $D_2$. Preferably, a settable and/or hardenable material 110 can be injected and/or otherwise introduced into a space "S" defined by frame 100 and end plates $E_1$ and $E_2$.

In particular, frame 100 encircles (e.g., frame 100 preferably surrounds the perimeter of settable material 110 while end plates $E_1$ and $E_2$ bound the areas above and below settable material 110) settable material 110 while settable material 110 cures and/or hardens. In this manner, settable material 110 directly engages (physically and/or biologically) end plates $E_1$ and $E_2$. Frame 100 can be a permanent implant between vertebral discs $D_1$ and $D_2$ or, in the alternative, frame 100 can be removed from between vertebral discs $D_1$ and $D_2$ following the hardening and/or curing of settable material 110. As will be illustrated in greater detail below, frame 100 can be rigid, semi-rigid, flexible or any combination thereof. For example, frame 100 can be constructed from a metal (e.g., titanium, Titanium alloy, steel, shape memory alloys, etc., resorbable and non-resorbable polymers, ceramics, organic materials, or any combination thereof.

Settable material 110 includes any type of biocompatible load bearing material or substance including bone composites, polymers of bone growth material or any biocompatible material or substance, which stabilizes, controls, regulates, promotes or accelerates new bone growth, bone healing and/or bone remodeling to thereby fuse the adjacent end plates. This may be a result of some osteogenic, osteoconductive and/or osteoinductive effect of the bone graft material.

Examples of bone growth materials which can be incorporated into the implants disclosed in this application include, e.g., collagen, insoluble collagen derivatives, etc., and soluble solids and/or liquids dissolved therein, e.g., antiviral agents, particularly those effective against HIV and hepatitis; antimicrobials, antibiotics and/or antimycotics such as erythromycin, bacitracin, neomycin, penicillin, polymyxin B, tetracyclines, viomycin, chloromycetin and streptomycins, cefazolin, ampicillin, azactam, tobramycin, clindamycin and gentamicin, etc.; biocidal/biostatic sugars such as dextrose, glucose, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with parenchymal cells; angiogenic drugs and polymeric carriers containing such drugs; collagen lattices; antigenic agents; cytoskeletal agents; cartilage fragments, living cells such as chondrocytes, bone marrow cells, mesenchymal stem cells, natural extracts, tissue transplants, bone, demineralized bone, partially demineralized bone, mineralized bone, bone graft substitutes such as hydroxylapatite, tricalcium phosphate, polycrystalline calcium, calcium carbonate, coralline calcium, calcium phosphate, calcium hydrogen phosphate, calcium phosphosilicate, tetrabasic calcium phosphate, sodium chondroitin sulfate, sodium succinate anhydride, calcium sulfate, magnesium stearate, calcium sulfate dihydrate, polyvinyl pyrilodone, propylene glycol-Co-Fumaric acid, calcified polyurethane, baria-boroalumino-silicate glass, polylactide-co-glycolide, autogenous tissues such as blood, serum, soft tissue, bone marrow, etc.; bioadhesives, bone morphogenic proteins (BMPs), transforming growth factor (TGF-beta), insulin-like growth factor (IGF-1); growth hormones such as estrogen and sonatotropin; bone digestors; antitumor agents; immunosuppressants; angiogenic agents such as basic fibroblast growth factor (bFGF); permeation enhancers, e.g., fatty acid esters such as laureate, myristate and stearate monoesters of polyethylene glycol, enamine derivatives, alpha-keto aldehydes, etc.; and, nucleic acids. In certain embodiments, the implant may be filled or loaded with any piece of bone including; cortical, cancellous and cortico-cancellous bone of autogenic, allogenic or xenogenic origin, and any combinations thereof.

Autogenic bone is bone harvested from the patient's own skeletal system, e.g., the iliac crest and grafts made of autogenic bone are referred to as "autografts". Allogenic bone is bone harvested from the skeletal system of another human source and grafts made from allogenic bone are referred to as "allografts". Typically, allogenic bone is harvested from cadavers and treated and stored in a bone bank until it is ultimately needed for implantation. Allogenic bone and autogenic bone are resorbable and are known to have osteoconductive and osteoinductive capabilities and, thus, are desirable for implant use.

Figure 2:
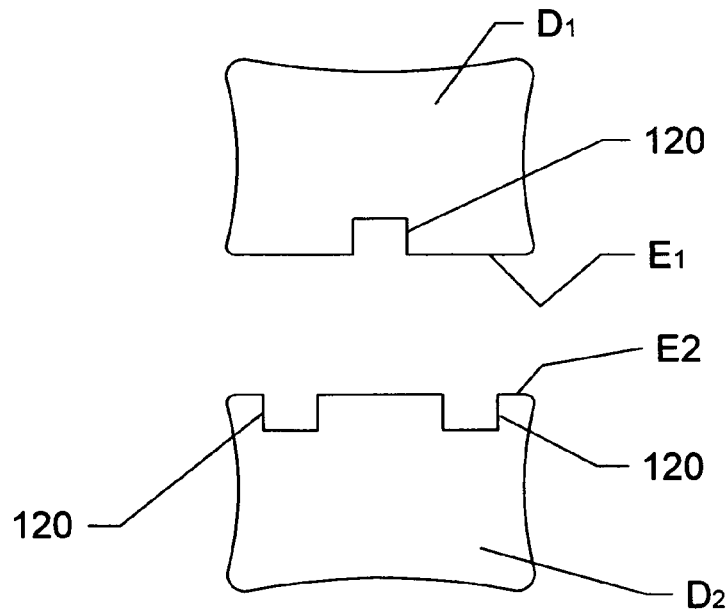
FIG. 2 is a cross-sectional view of the vertebral discs of FIG. 1 as taken along 2-2 of FIG. 1 illustrating recesses/grooves formed therein.
Figure 3:
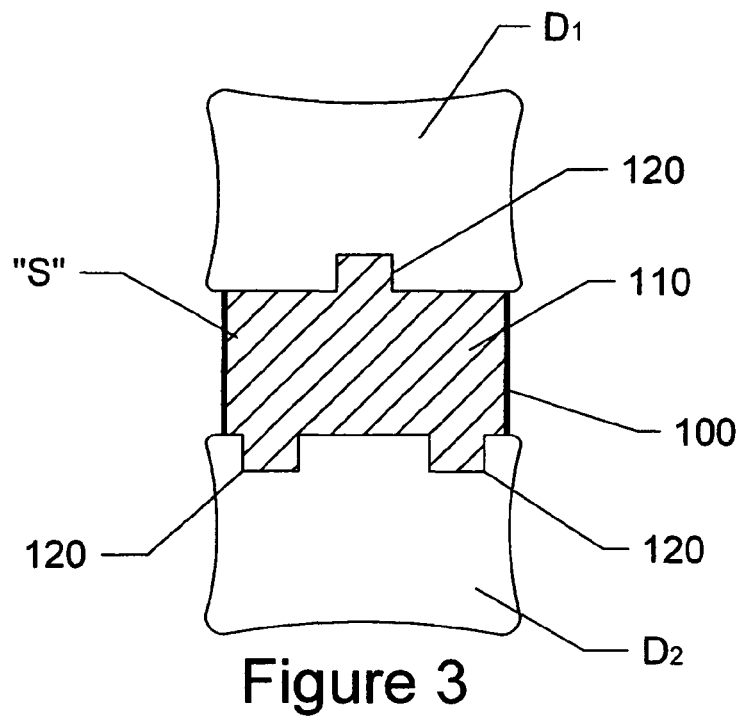
FIG. 3 is a cross-sectional view of the vertebral discs of FIG. 1 as taken along 2-2 of FIG. 1 illustrating the placement of a frame filled with settable material positioned in the space between the adjacent vertebral discs.

As seen in FIGS. 2-16, during a surgical procedure, end plates $E_1$ and $E_2$ of vertebral discs $D_1$ and $D_2$ are prepared and/or formed, using known surgical techniques, e.g., to define keyed grooves 120 (see FIG. 2) therein. The goal of this end plate preparation and forming is two-fold. One is to expose bleeding bone to enhance the fusion process, and two is to enhance the securement of the implant to the endplate to increase the stability of the construct so that fusion will occur. Prior to, concomitant with, or following preparation of end plates $E_1$ and $E_2$, frame 100 is inserted between end plates $E_1$ and $E_2$ in such a manner so as to at least substantially surround the prepared surfaces of end plates $E_1$ and $E_2$, e.g., grooves 120 formed therein.

Subsequently, the space defined by frame 100 and end plates $E_1$ and $E_2$ is filled with settable material 110. As such, settable material 110 enters into grooves 120 which in turn promote and/or increase the anchoring effect of settable material to end plates $E_1$ and $E_2$ and subsequently result in the fusion of the vertebral motion segment.

Figure 4:
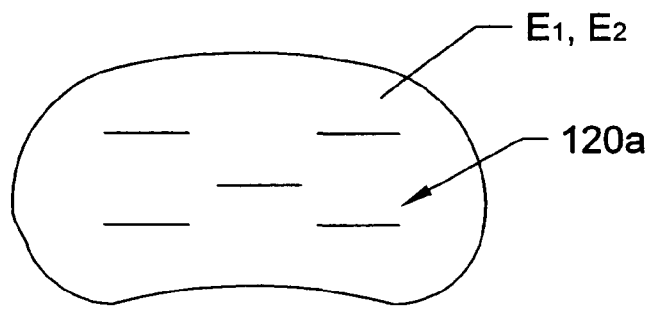
FIG. 4 is a top plan view of a vertebral disc of FIG. 1 illustrating an exemplary arrangement of the recesses/grooves formed in the end plate thereof.
Figure 5:
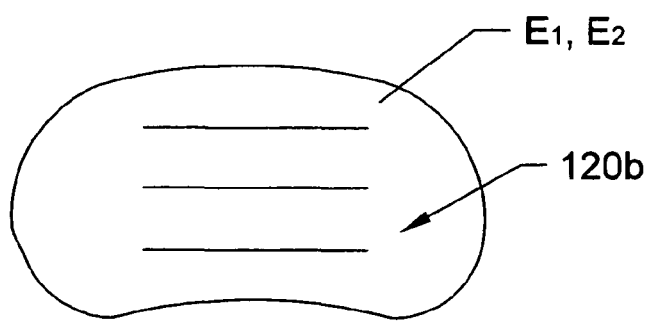
FIG. 5 is a top plan view of a vertebral disc of FIG. 1 illustrating another exemplary arrangement of the recesses/grooves formed in the end plate thereof.
Figure 6:
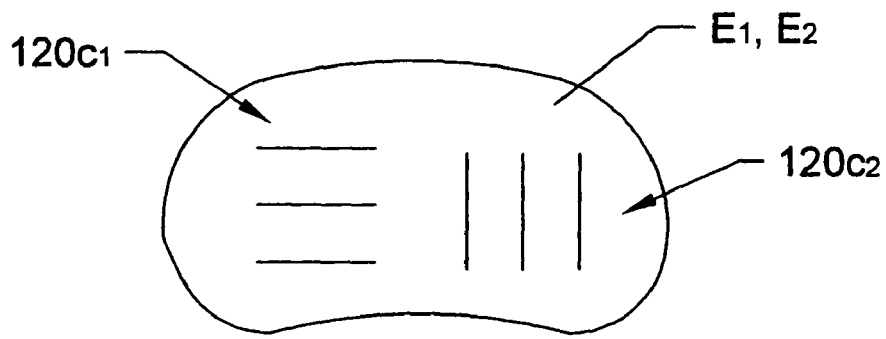
FIG. 6 is a top plan view of a vertebral disc of FIG. 1 illustrating yet another exemplary arrangement of the recesses/grooves formed in the end plate thereof.
Figure 7:
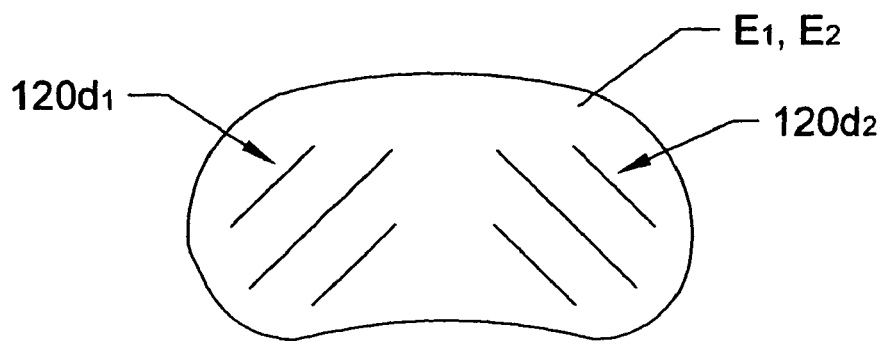
FIG. 7 is a top plan view of a vertebral disc of FIG. 1 illustrating a further exemplary arrangement of the recesses/grooves formed in the end plate thereof.
Figure 8:
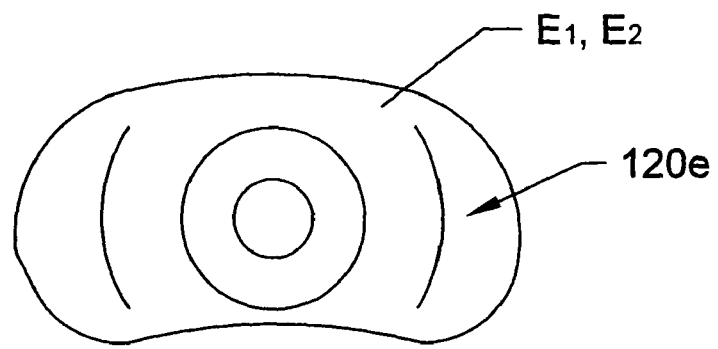
FIG. 8 is a top plan view of a vertebral disc of FIG. 1 illustrating still a further exemplary arrangement of the recesses/grooves formed in the end plate thereof.

Turning now to FIGS. 4-8 various configurations for grooves 120 formed in end plates $E_1$ and $E_2$ are shown. In FIG. 4, at least one end plate $E_1$, $E_2$ includes discontinuous linear grooves 120a arranged in a cross configuration. In FIG. 5, at least one end plate $E_1$, $E_2$ includes continuous linear grooves 120a extending substantially completely thereacross. In FIG. 6, at least one end plate $E_1$, $E_2$ includes a first set of linear grooves $120c_1$ extending longitudinally across a first half of end plate $E_1$ and/or $E_2$ and a second set of linear grooves $120c_2$ extending transversely across a second half of end plate $E_1$ and/or $E_2$. In FIG. 7, at least one end plate $E_1$, $E_2$ includes a first set of linear grooves $120d_1$ extending angularly across a first half of end plate $E_1$ and/or $E_2$ and a second set of linear grooves $120d_2$ extending angularly across a second half of end plate $E_1$ and/or $E_2$. In FIG. 8, at least one end plate $E_1$, $E_2$ includes a series of concentric circular and arcuate grooves 120e. It is envisioned and within the scope of the present disclosure that any combination of configurations is possible.

Figure 9:
FIG. 9 is a cross-sectional view of a vertebral disc of FIG. 1 illustrating an exemplary profile of the surface of the end plate thereof.
Figure 10:
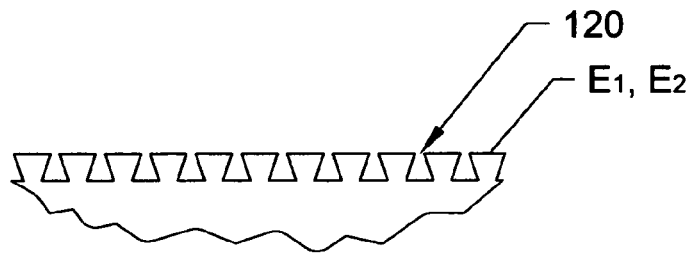
FIG. 10 is a cross-sectional view of a vertebral disc of FIG. 1 illustrating another exemplary profile of the surface of the end plate thereof.
Figure 11:
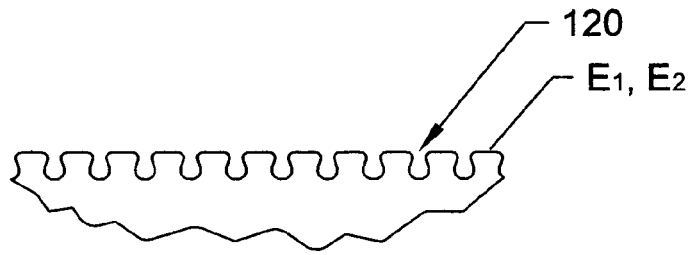
FIG. 11 is a cross-sectional view of a vertebral disc of FIG. 1 illustrating yet another exemplary profile of the surface of the end plate thereof.
Figure 12:
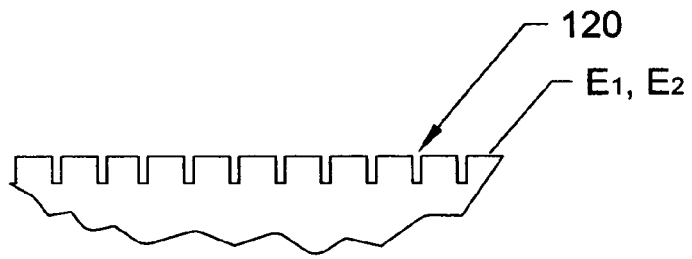
FIG. 12 is a cross-sectional view of a vertebral disc of FIG. 1 illustrating still another exemplary profile of the surface of the end plate thereof.
Figure 13:
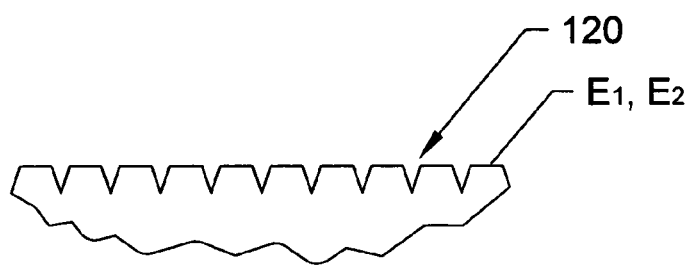
FIG. 13 is a cross-sectional view of a vertebral disc of FIG. 1 illustrating a further exemplary profile of the surface of the end plate thereof.
Figure 14:
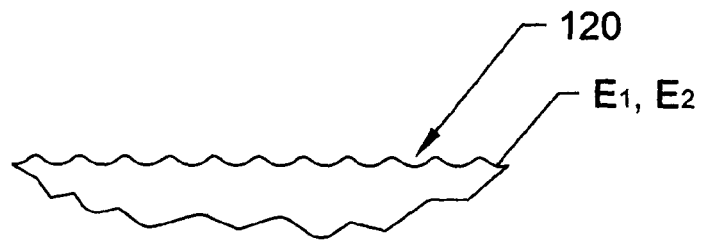
FIG. 14 is a cross-sectional view of a vertebral disc of FIG. 1 illustrating still a further exemplary profile of the surface of the end plate thereof.
Figure 15:
FIG. 15 is a cross-sectional view of a vertebral disc of FIG. 1 illustrating another exemplary profile of the surface of the end plate thereof.
Figure 16:
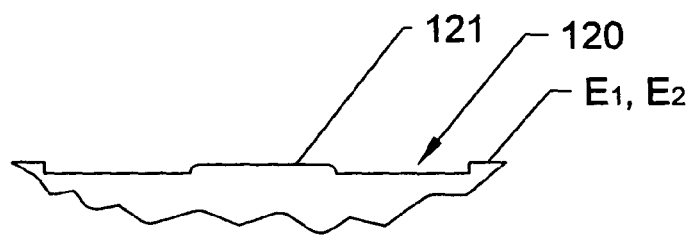
FIG. 16 is a cross-sectional view of a vertebral disc of FIG. 1 illustrating yet another exemplary profile of the surface of the end plate thereof.

Turning now to FIGS. 9-16 various topographical profiles for end plates $E_1$, $E_2$ and cross-sectional profiles for grooves 120 are shown. As seen in FIG. 9, at least one end plate $E_1$, $E_2$ can include a stepped topographical profile. As seen in FIG. 10, grooves 120 formed in at least one of end plates $E_1$, $E_2$ can be substantially trapezoidal in shape (e.g., dove tail). As seen in FIG. 11, grooves 120 formed in at least one of end plates $E_1$, $E_2$ can be substantially tear-dropped in shape. As seen in FIG. 12, grooves 120 formed in at least one of end plates $E_1$, $E_2$ can be substantially rectangular in shape. As seen in FIG. 13, grooves 120 formed in at least one of end plates $E_1$, $E_2$ can be substantially V-shaped. As seen in FIGS. 14 and 15, grooves 120 formed in at least one of end plates $E_1$, $E_2$ can be substantially wave-like in shape having rounded peaks (FIG. 14) or sharpened peaks (FIG. 15). As seen in FIG. 16, at least one of end plates $E_1$, $E_2$ can include a single groove 120 defining a recess in the surface thereof and a hump 121 formed therein.

Figure 17:
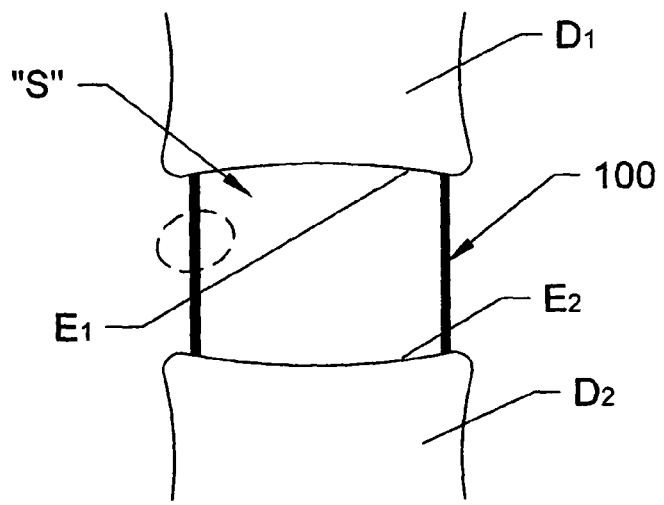
FIG. 17 is a cross-sectional view of the vertebral discs of FIG. 1 illustrating an exemplary method of supporting the frame between the vertebral discs.
Figure 18:
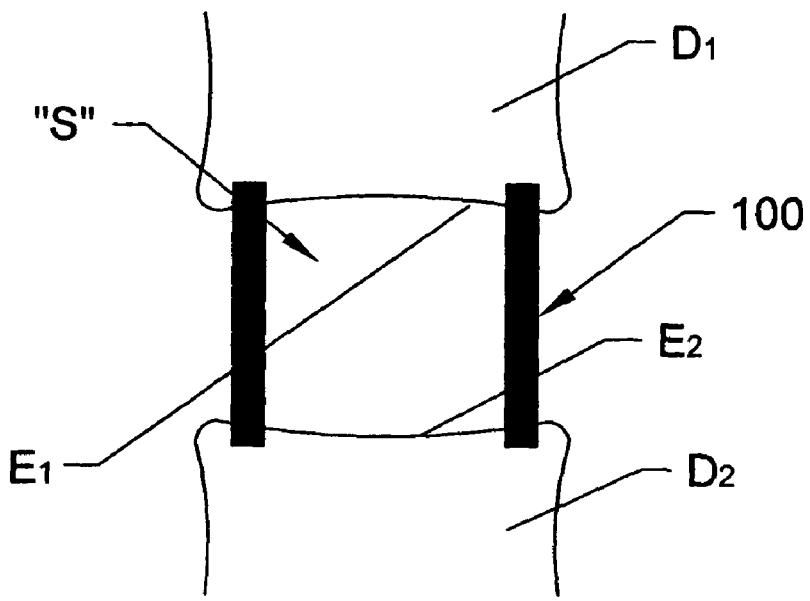
FIG. 18 is a cross-sectional view of the vertebral discs of FIG. 1 illustrating another exemplary method of supporting the frame between the vertebral discs.
Figure 19:
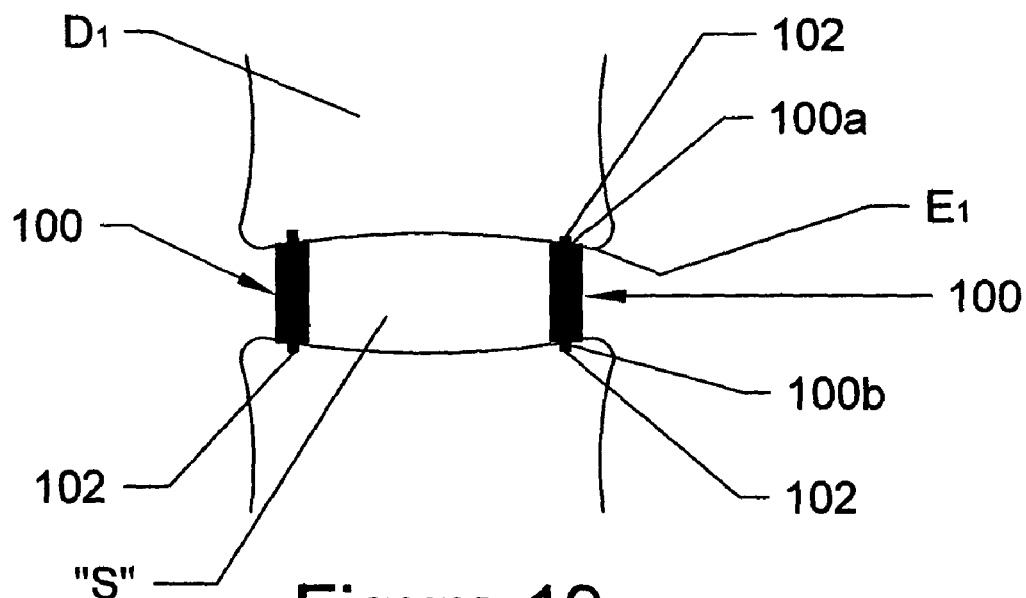
FIG. 19 is a cross-sectional view of the vertebral discs of FIG. 1 illustrating yet another exemplary method of supporting the frame between the vertebral discs.

Turning now to FIGS. 17-19 various arrangements for the engagement of frame 100 with end plates $E_1$, $E_2$ are provided. As seen in FIG. 17, frame 100 can rest flush against the surface of end plates $E_1$, $E_2$. As seen in FIG. 18, frame 100 can be at least partially imbedded in the surface of end plates $E_1$, $E_2$. As seen in FIG. 19, frame 100 can include a rim 102 formed along at least one of an upper edge 100a and a lower edge 100b thereof. As such, rim 102 can be imbedded in the surface of end plates $E_1$, $E_2$ while the remainder of frame 100 rests against the surface of end plates $E_1$, $E_2$.

Figure 20:
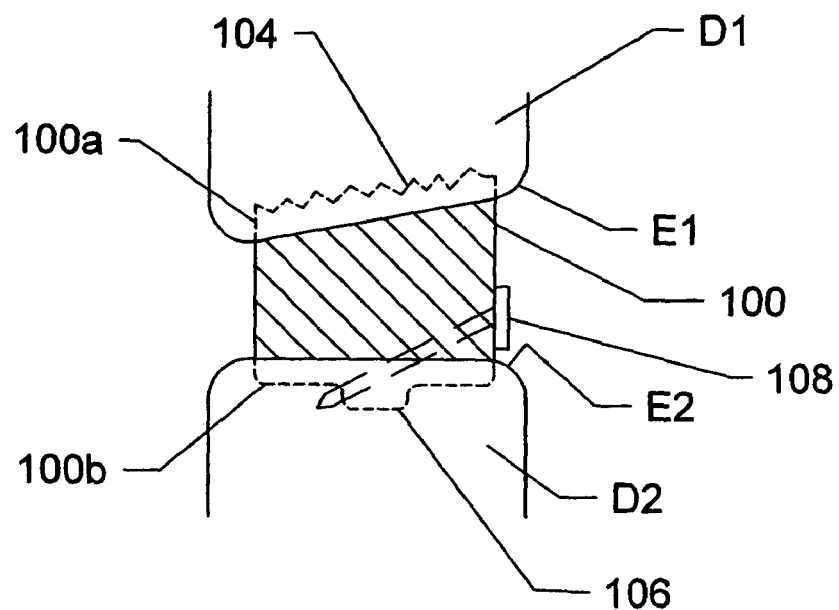
FIG. 20 is a side elevational view of the vertebral discs of FIG. 1 illustrating an exemplary method of securing the frame to at least one of the vertebral discs.
Figure 21:
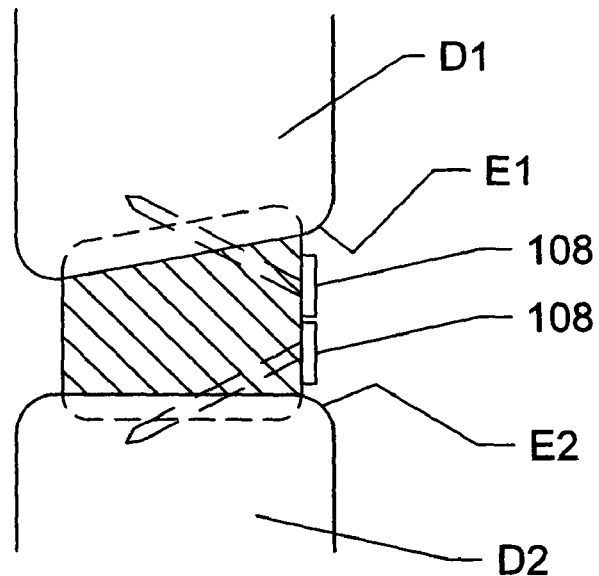
FIG. 21 is a side elevational view of the vertebral discs of FIG. 1 illustrating an exemplary method of securing the frame to each vertebral disc.

Turning now to FIGS. 20-23, various methods of fixedly securing frame 100 in position relative to end plates $E_1$, $E_2$ of vertebral discs $D_1$, $D_2$ are shown. This additional fixed securement will increase the stability of frame 100 with settable material 110 disposed therein, until fusion occurs. As seen in FIGS. 20 and 21, at least one screw 108 (e.g. a pedicle screw) is provided and extends through frame 100 at such an angle so as to be embedded in at least one of end plates $E_1$, $E_2$ of vertebral discs $D_1$, $D_2$. It is envisioned that upper edge 100a of frame 100 can be angled to approximate the angle of end plate $E_1$ of vertebral disc $D_1$ and can include a series of ridges 104 formed therealong to further secure frame 100 against end plate $E_1$ of vertebral disc $D_1$. In addition, lower edge 100b can include at least one tab 106 to further secure frame 100 against end plate $E_2$ of vertebral disc $D_2$.

Figure 22:
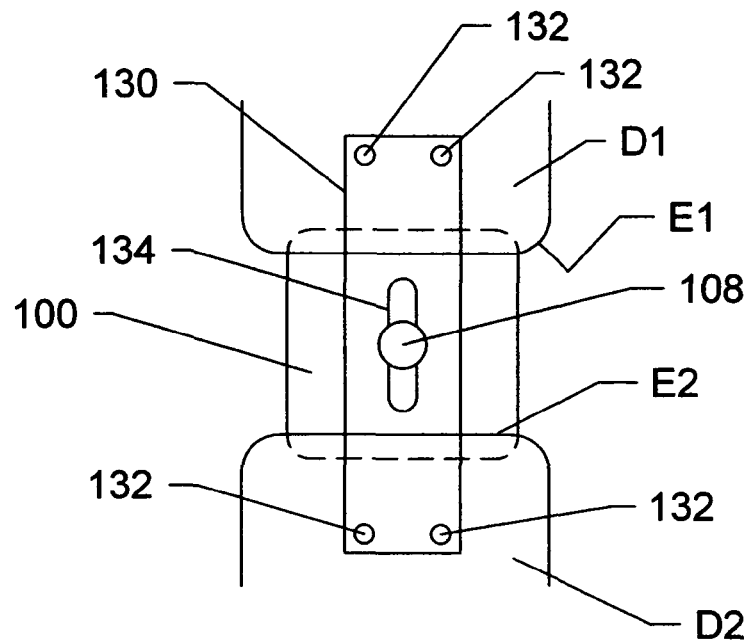
FIG. 22 is an anterior/posterior view of the vertebral discs of FIG. 1 illustrating an alternative method of securing the frame between the vertebral discs.
Figure 23:
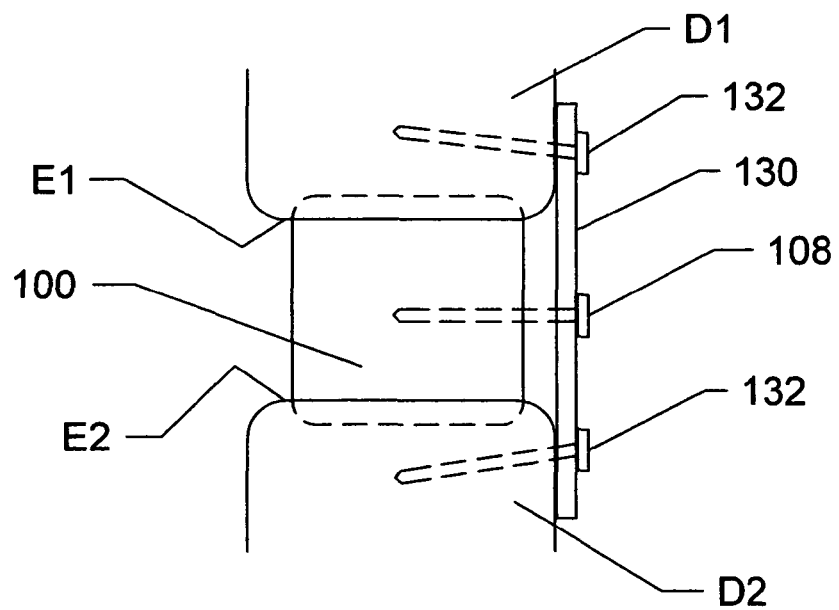
FIG. 23 is a side elevational view of the vertebral discs of FIG. 22 illustrating the method of securing the frame therebetween.

As seen in FIGS. 22 and 23, a support plate 130 can be provided which extends from vertebral disc $D_1$ to vertebral disc $D_2$. Support plate 130 can be secured to vertebral discs $D_1$ and $D_2$ by screws 132 and the like. Meanwhile, a screw 108 is provided which extends through support plate 130 and is embedded in frame 100. Support plate 130 can include an elongate slot 134 formed therein through which screw 108 passes. In this manner, screw 108 can be positioned anywhere along elongate slot 134 in order to be better received in the aperture formed in frame 100.

As will be described in greater detail below, screws 108 can be received in apertures (not shown) formed in frame 100 which are or can be used for the injection of settable material 110 into frame 100. In this manner, placement of screw 108 into such aperture effectively closes the aperture and inhibits escape of settable material 110 from frame 100.

Figure 24:
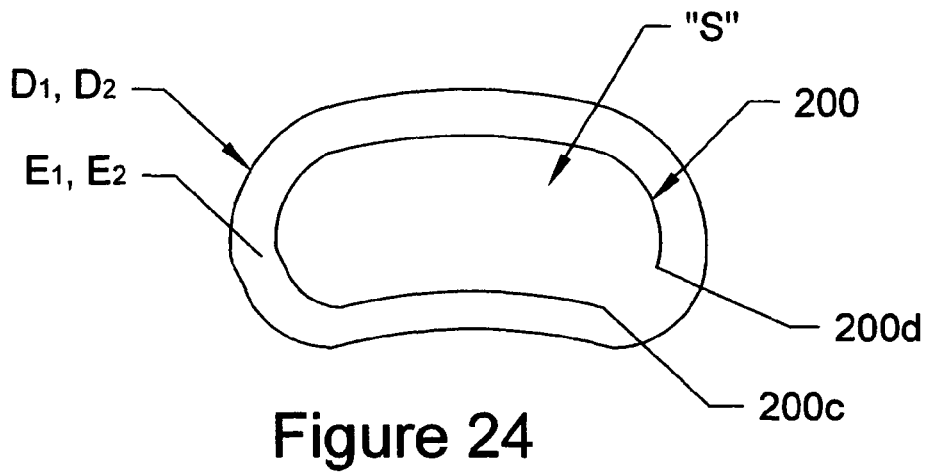
FIG. 24 is a top plan view of a vertebral disc of FIG. 1 illustrating an initial stage in the placement of a frame between the vertebral discs.
Figure 25:
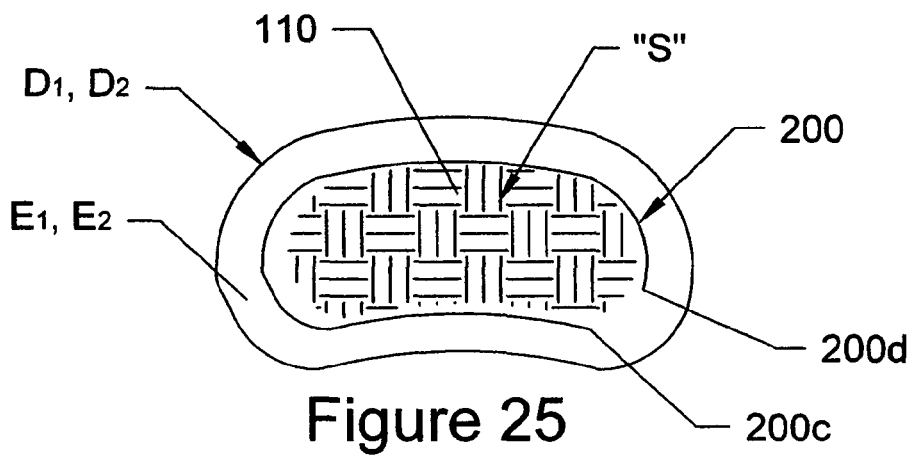
FIG. 25 is a top plan view of the vertebral disc of FIG. 24 illustrating a subsequent stage in the placement of the frame between the vertebral discs.
Figure 26:
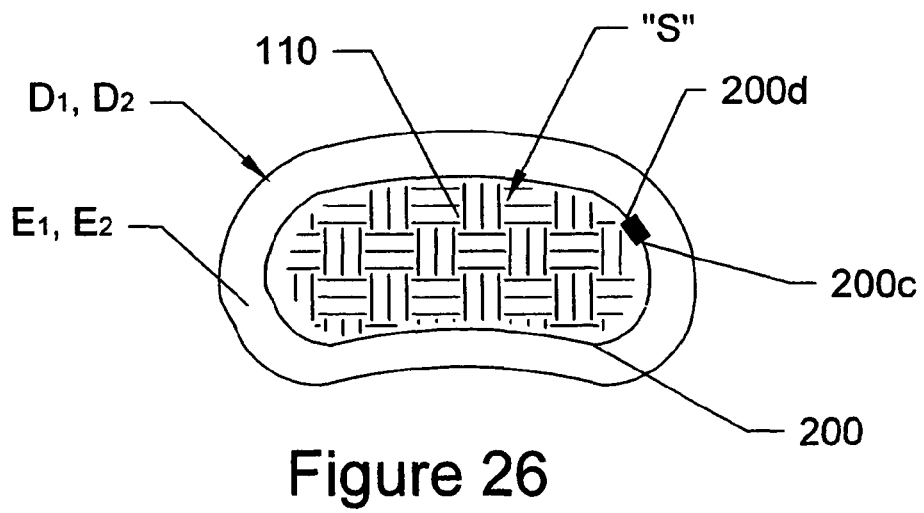
FIG. 26 is a top plan view of the vertebral disc of FIGS. 24 and 25 illustrating a further subsequent stage in the placement of the frame between the vertebral discs.

Turning now to FIGS. 24-26, an exemplary method of placing a frame and settable material between end plates $E_1$, $E_2$ of vertebral discs $D_1$, $D_2$ is shown. As seen in FIG. 24, a band or ribbon-like frame 200, including a distal end 200c and a proximal end 200d, is inserted between end plates $E_1$, $E_2$ of vertebral discs $D_1$, $D_2$ such that frame 200 substantially approximates the outer perimeteral profile of end plates $E_1$, $E_2$ and such that distal end 200c is brought in close proximity to proximal end 200d. As seen in FIG. 25, with frame 200 so positioned, settable material 110 is introduced into space "S" bounded by frame 200 and end plates $E_1$, $E_2$. With settable material 110 injected into space "S", distal end 200c and proximal end 200d are secured to one another using known techniques, such as for example, screwing, riveting, welding, adhering, buckling and the like, to thereby contain settable material within space "S".

Figure 27:
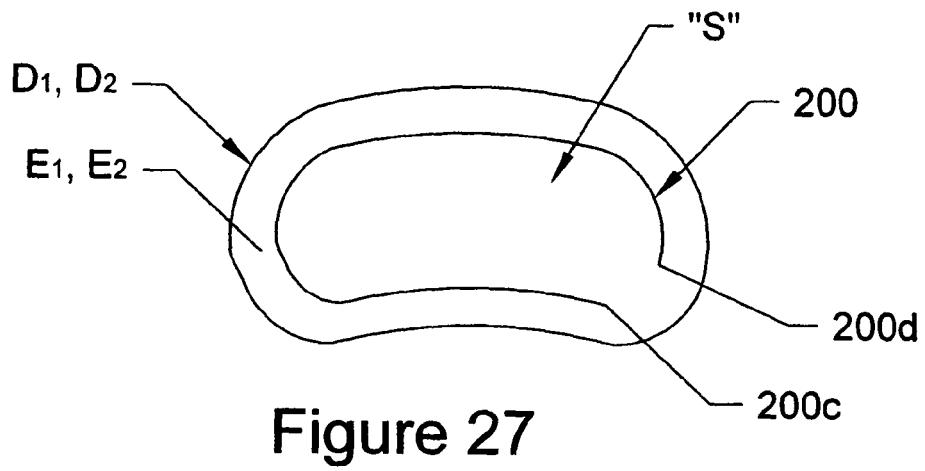
FIG. 27 is a top plan view of a vertebral disc of FIG. 1 illustrating an initial stage in the placement of a frame between the vertebral discs.
Figure 28:
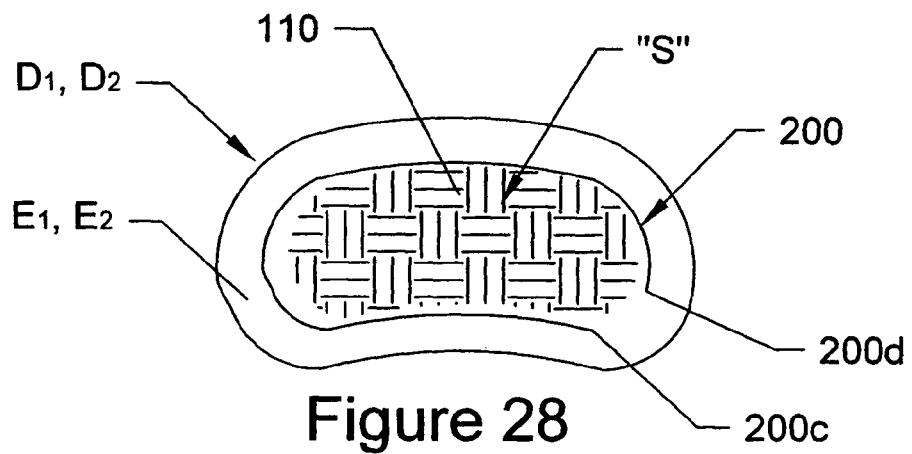
FIG. 28 is a top plan view of the vertebral disc of FIG. 27 illustrating a subsequent stage in the placement of the frame between the vertebral discs.
Figure 29:
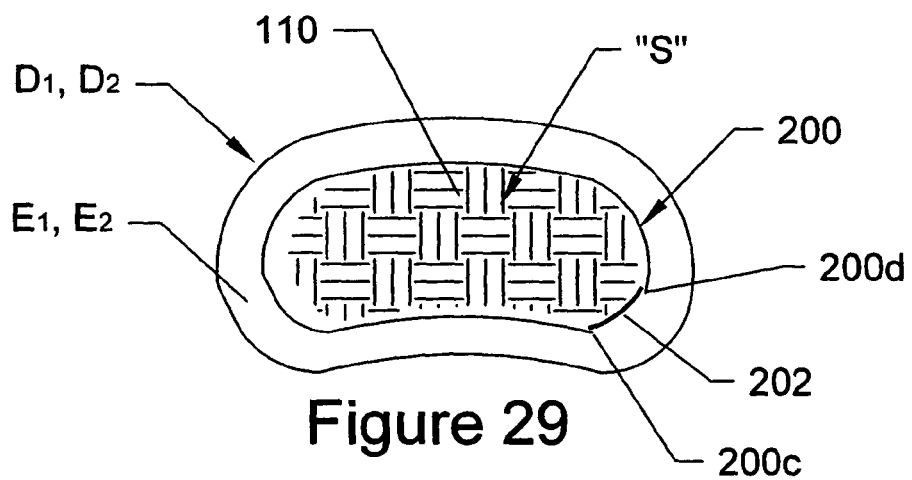
FIG. 29 is a top plan view of the vertebral disc of FIGS. 27 and 28 illustrating a further subsequent stage in the placement of the frame between the vertebral discs.

Turning now to FIGS. 27-29, another exemplary method of placing a frame and settable material between end plates $E_1$, $E_2$ of vertebral discs $D_1$, $D_2$ is shown. As seen in FIG. 27, frame 200 is inserted between end plates $E_1$, $E_2$ of vertebral discs $D_1$, $D_2$ such that frame 200 substantially approximates the outer perimeteral profile of end plates $E_1$, $E_2$ and such that distal end 200c is brought in close proximity to proximal end 200d. As seen in FIG. 28, with frame 200 so positioned, settable material 110 is introduced into space "S" bounded by frame 200 and end plates $E_1$, $E_2$. With settable material 110 injected into space "S", a cap 202 is placed in position between distal end 200c and proximal end 200d of frame 200 so as to contain settable material 110 in space "S".

Figure 30:
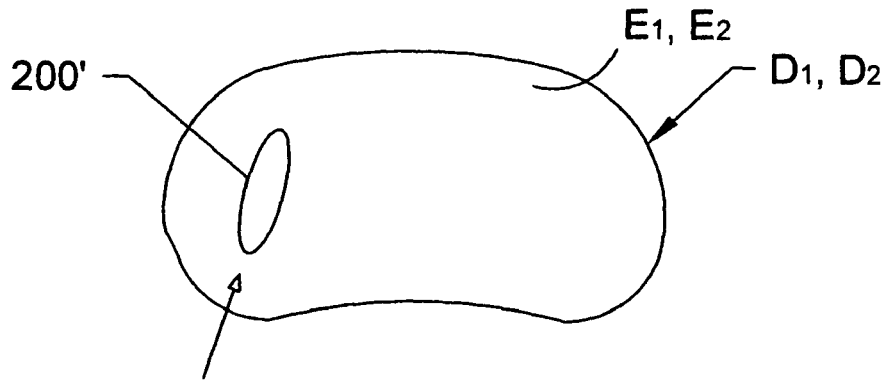
FIG. 30 is a top plan view of a vertebral disc of FIG. 1 illustrating an initial stage in the placement of a first frame between the vertebral discs.
Figure 31:
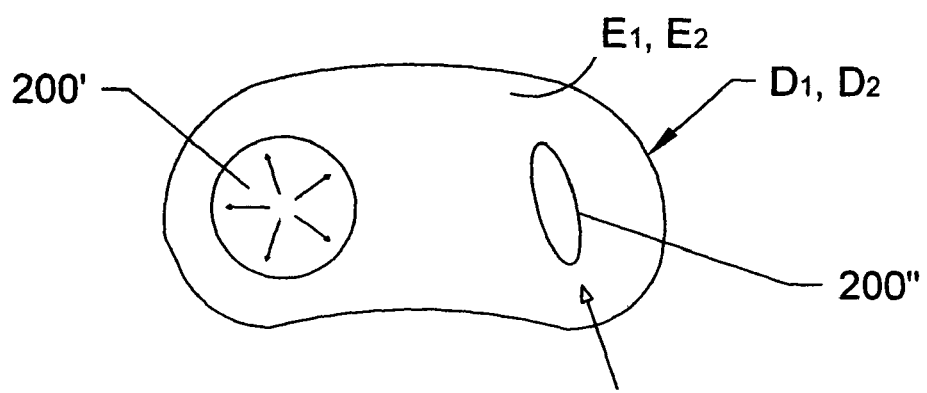
FIG. 31 is a top plan view of the vertebral disc of FIG. 30 illustrating a subsequent stage in the placement of the first frame between the vertebral discs and the placement of a second frame between the vertebral discs.
Figure 32:
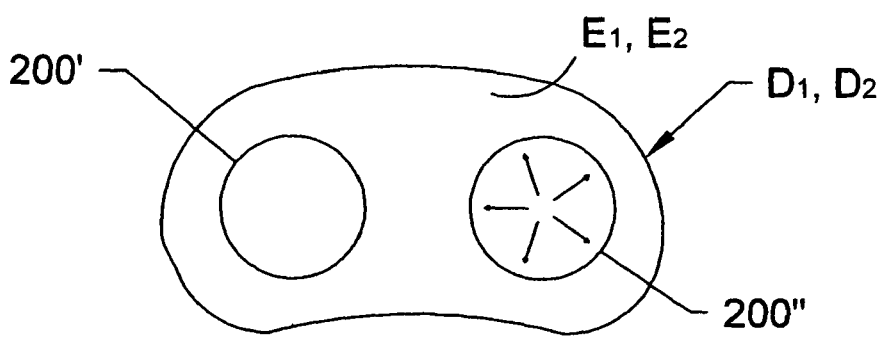
FIG. 32 is a top plan view of the vertebral disc of FIGS. 31 and 32 illustrating a subsequent stage in the placement of the second frame between the vertebral discs.

Turning now to FIGS. 30-32, an exemplary method of positioning a number of frames 200 between end plates $E_1$, $E_2$ of vertebral discs $D_1$, $D_2$ is shown. As seen in FIG. 30, a first frame 200', having a relatively small foot print, is introduced between end plates $E_1$, $E_2$ of vertebral discs $D_1$, $D_2$. As seen in FIG. 31, first frame 200' is expanded to have a relatively larger foot print than its original insertion foot print. A second frame 200", having a relatively small foot print, is then introduced between end plates $E_1$, $E_2$ of vertebral discs $D_1$, $D_2$. As seen in FIG. 32, second frame 200' is expanded to have a relatively larger foot print than its original insertion foot print. In this manner, frames 200' and 200" are manipulated and/or sized to substantially fill the inner boundary of vertebral discs $D_1$, $D_2$.

Figure 33:
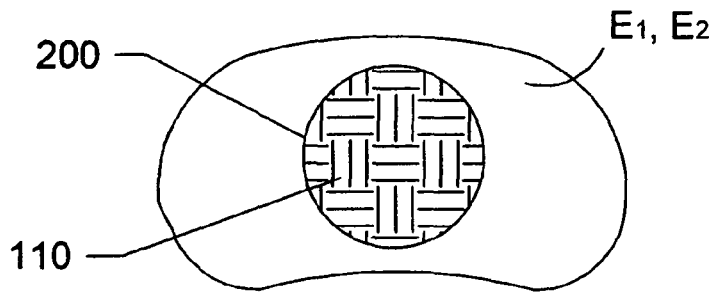
FIG. 33 is a top plan view of a vertebral disc of FIG. 1 illustrating an exemplary configuration and placement of the frame between the vertebral discs.
Figure 34:
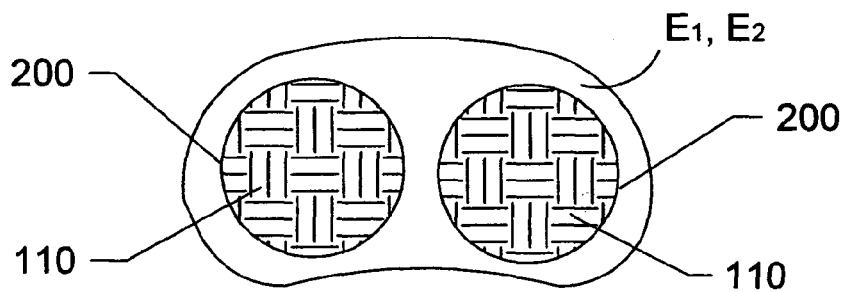
FIG. 34 is a top plan view of a vertebral disc of FIG. 1 illustrating another exemplary configuration and placement of the frame between the vertebral discs.
Figure 35:
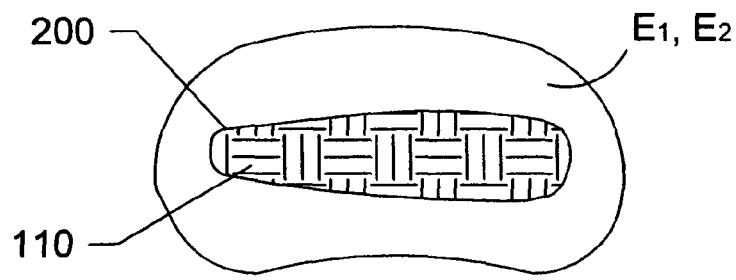
FIG. 35 is a top plan view of a vertebral disc of FIG. 1 illustrating yet another exemplary configuration and placement of the frame between the vertebral discs.
Figure 36:
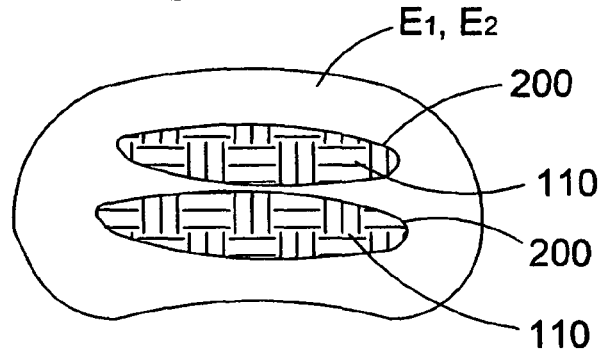
FIG. 36 is a top plan view of a vertebral disc of FIG. 1 illustrating still another exemplary configuration and placement of the frame between the vertebral discs.
Figure 37:
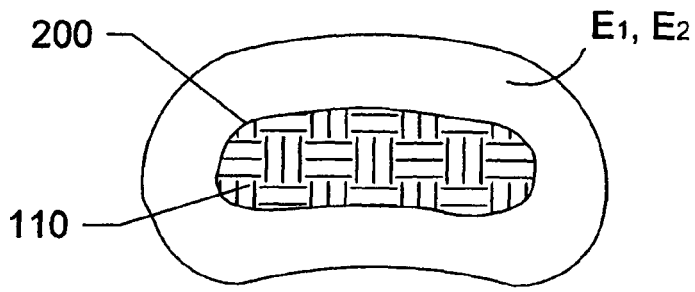
FIG. 37 is a top plan view of a vertebral disc of FIG. 1 illustrating a further exemplary configuration and placement of the frame between the vertebral discs.

Turning now to FIGS. 33-44, various configurations and placements of frames 200 between end plates $E_1$, $E_2$ of vertebral discs $D_1$, $D_2$ are shown. As seen in FIG. 33, frame 200 can be substantially circular and centrally located between end plates $E_1$, $E_2$ of vertebral discs $D_1$, $D_2$. As seen in FIG. 34, a pair of substantially circular frames 200 can be positioned between end plates $E_1$, $E_2$ of vertebral discs $D_1$, $D_2$ such that substantially the entire foot print of end plates $E_1$, $E_2$ is filled. As seen in FIGS. 35 and 36, at least one frame 200, having an elongate configuration, is provided and extends substantially across the entire foot print of end plates $E_1$, $E_2$. As seen in FIG. 37, frame 200 substantially conforms in shape to the perimeteral contour of end plates $E_1$, $E_2$.

Figure 38:
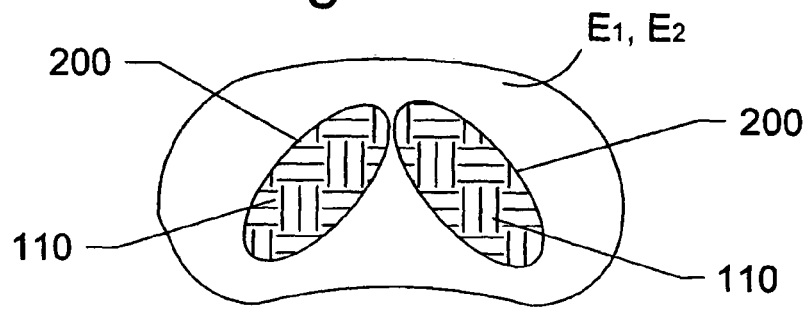
FIG. 38 is a top plan view of a vertebral disc of FIG. 1 illustrating an additional exemplary configuration and placement of the frame between the vertebral discs.
Figure 39:
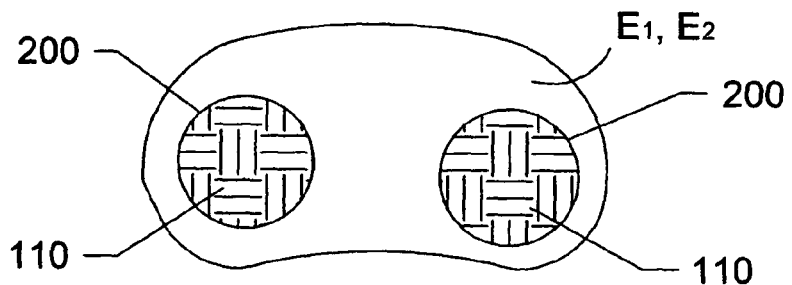
FIG. 39 is a top plan view of a vertebral disc of FIG. 1 illustrating another exemplary configuration and placement of the frame between the vertebral discs.
Figure 40:
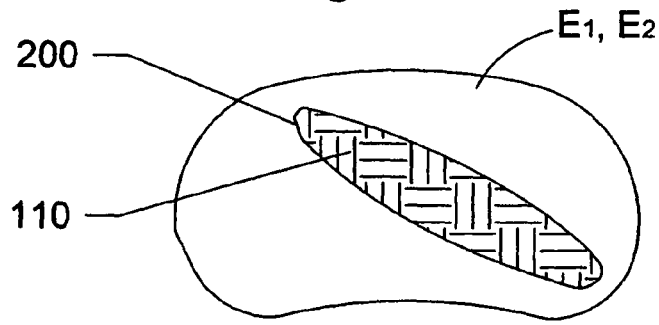
FIG. 40 is a top plan view of a vertebral disc of FIG. 1 illustrating yet another exemplary configuration and placement of the frame between the vertebral discs.

As seen in FIG. 38, a pair of ovular frames 200 is provided which are proximate one another near the anterior or posterior region of vertebral discs $D_1$, $D_2$ and spaced from one another near the other of the anterior or posterior region of vertebral discs $D_1$, $D_2$. As seen in FIG. 39, a pair of substantially circular frames 200 is provided which are each sized to be relatively smaller than the circular frames shown in FIG. 34. As seen in FIG. 40, an elliptical frame 200 extending diagonally across end plates $E_1$, $E_2$ is provided.

Figure 41:
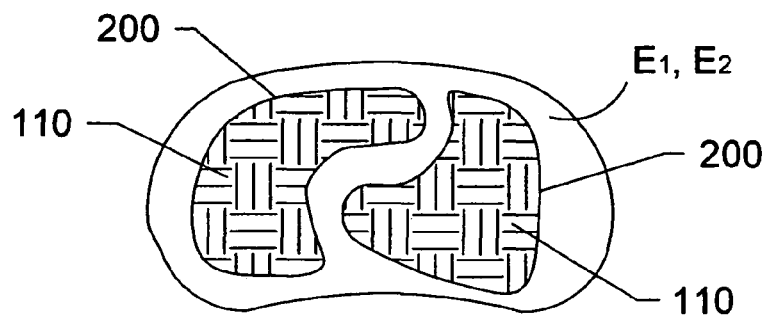
FIG. 41 is a top plan view of a vertebral disc of FIG. 1 illustrating still another exemplary configuration and placement of the frame between the vertebral discs.
Figure 42:
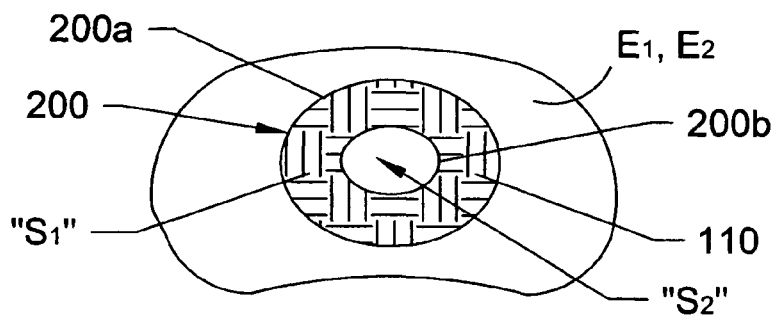
FIG. 42 is a top plan view of a vertebral disc of FIG. 1 illustrating a further exemplary configuration and placement of the frame between the vertebral discs.

In FIG. 41, a pair of adjacent frames 200, each having a substantially crescent shape, can be provided between end plates $E_1$, $E_2$. As seen in FIG. 42, a pair of frames 200 can be provided between end plates $E_1$, $E_2$, wherein an outer frame 200a surrounds an inner frame 200b. Accordingly, it is envisioned that settable material 110 can be provided solely in the space "$S_1$" between frames 200a, 200b, solely in the space "$S_2$" defined by inner frame 200b or in both spaces "$S_1$ and $S_2$".

Figure 43:
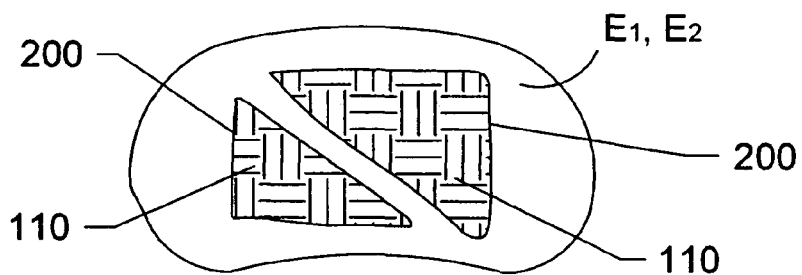
FIG. 43 is a top plan view of a vertebral disc of FIG. 1 illustrating an additional exemplary configuration and placement of the frame between the vertebral discs.
Figure 44:
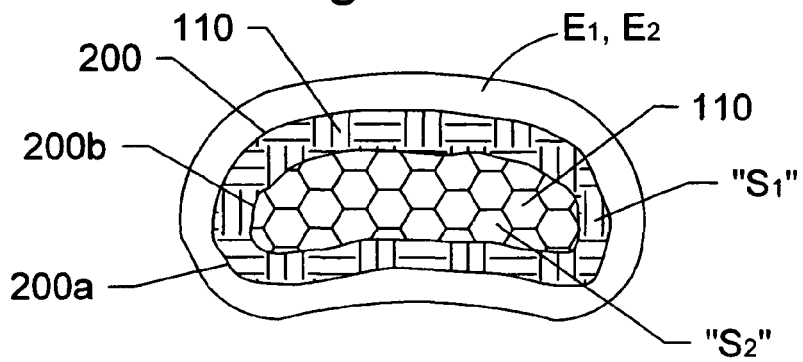
FIG. 44 is a top plan view of a vertebral disc of FIG. 1 illustrating another exemplary configuration and placement of the frame between the vertebral discs.

As seen in FIG. 43, a pair of frames 200, each substantially triangular in shape, can be provided between end plates $E_1$, $E_2$. As seen in FIG. 44, a pair of frames 200, including an outer frame 200a and an inner frame 200b each being substantially crescent shaped, can be provided between end plates $E_1$, $E_2$. Accordingly, it is envisioned that settable material 110 can be provided solely in the space "$S_1$", between frames 200a, 200b, solely in the space "$S_2$" defined by inner frame 200b or in both spaces "$S_1$ and $S_2$".

Figure 45:
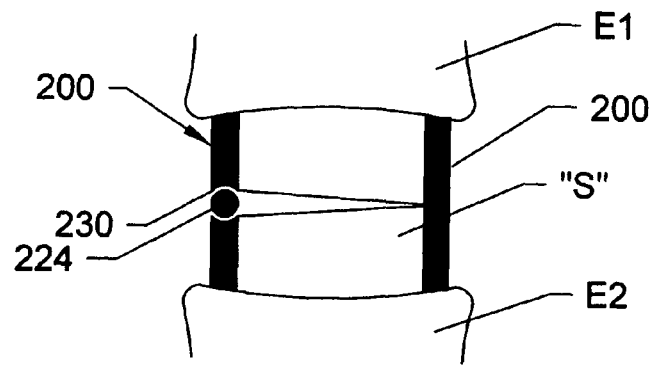
FIG. 45 is a cross-sectional side elevational view of the vertebral discs of FIG. 1 illustrating an exemplary frame disposed therebetween.

Turning now to FIG. 45, a substantially cylindrical ribbon or band-like frame 200 having an aperture 230 formed therein, can be provided. As seen in FIG. 45, a ball or plug 224 can be provided for closing aperture 230 following introduction of settable material 110 into space "S" bounded by frame 200 and end plates $E_1$, $E_2$. Preferably, aperture 230 is shaped (e.g., provided with a concave radial profile) and ball 224 is sized to be snap-fit into and retained therein.

Figure 46:
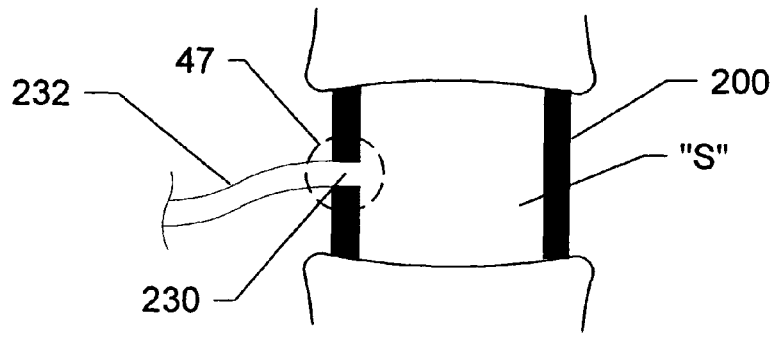
FIG. 46 is a cross-sectional side elevational view of the vertebral discs of FIG. 1 illustrating an exemplary arrangement for injecting settable material into the space defined by the frame and the adjacent vertebral discs.

As seen in FIG. 46, frame 200 can be provided with at least one aperture 230 formed therein. In this manner, a conduit 232 can be coupled to frame 200, such that conduit 232 is in fluid communication with aperture 230. As such, settable material 110 can be injected into space "S" of frame 200 through conduit 232 and aperture 230. Following injection of settable material 110 into space "S" of frame 200, conduit 232 can be tied off, twisted, knotted, heat sealed and the like. While a conduit 232 has been shown and described, it is envisioned, and within the scope of the present disclosure, that settable material 110 can by injected into space "S" using any number of systems, devices and the like. For example, a syringe (not shown) can be used to fill space "S" with settable material 110 by inserting the tip of the needle of the syringe into aperture 230 formed in frame 200. Other devices which can be used to introduce settable material 110 into space "S" include and are not limited to, catheters, funnels, pumps and the like.

Figure 47:
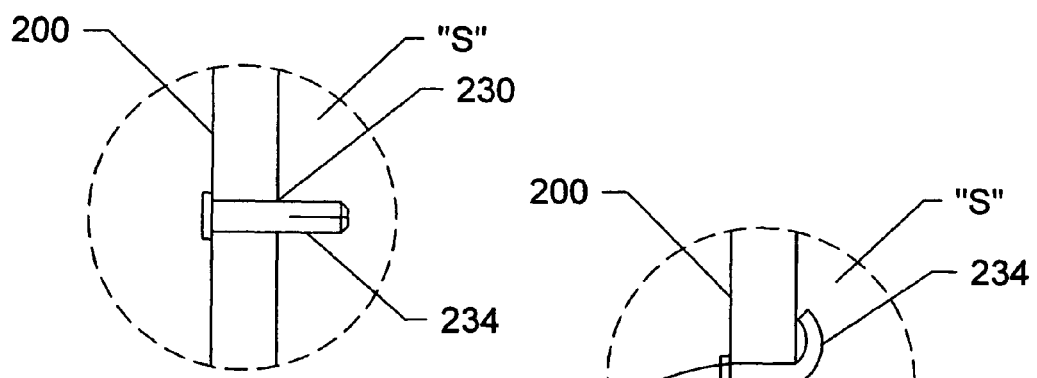
FIG. 47 is an enlarged view of the area indicated as 46 in FIG. 46 illustrating a stage in the closure of the aperture formed in the frame.
Figure 48:
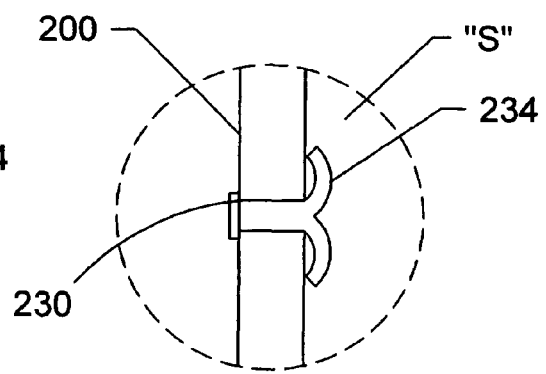
FIG. 48 is an enlarged view of the area indicated as 46 in FIG. 46 illustrating another stage in the closure of the aperture formed in the frame.

As seen in FIGS. 47 and 48, following injection of settable material 110 into space "S", aperture 230 can be closed and/or plugged, to thereby prevent the escape of settable material 110 from space "S" of frame 200, by inserting a rivet 234 into aperture 230 (FIG. 47) and deforming rivet 234 to thereby anchor rivet 234 against frame 200 and effectively occlude aperture 230. While rivet 234 has been shown and described, any device for occluding aperture 230 can be used, such as, for example, a screw, a cork, a plug, a plate or the like. A fluid tight seal between rivet 234 and frame 200 is not necessary if settable material 110 which is relatively more viscous is injected into space "S" of frame 200. Aperture 230 can also be occluded by applying direct pressure over aperture 230 for a time sufficient for settable material 110 to begin to cure or in the case that settable material 110 is photo-curable, by applying light into aperture 230.

Figure 49:
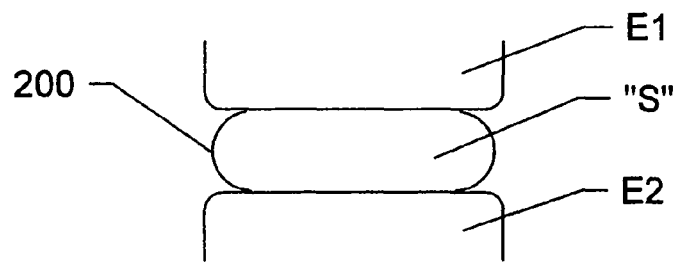
FIG. 49 is a cross-sectional side elevational view illustrating the positioning of a frame between a pair of compressed vertebral discs.
Figure 50:
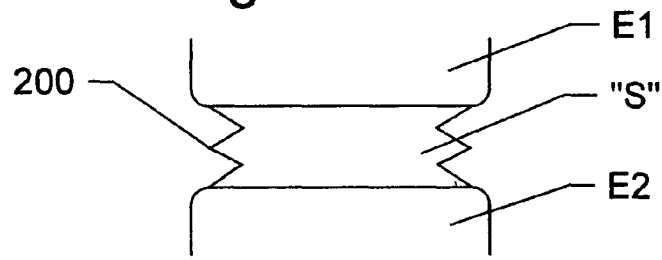
FIG. 50 is a cross-sectional side elevational view illustrating the positioning of another frame between a pair of compressed vertebral discs.
Figure 51:
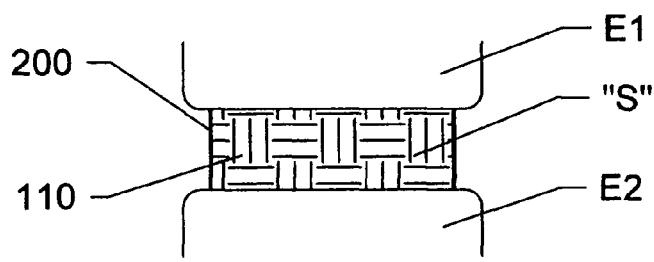
FIG. 51 is a cross-sectional side elevational view of the vertebral discs of FIGS. 49 and 50 following injection of a settable material into the space defined by the adjacent vertebral discs and the frames of FIGS. 49 and 50.

Turning now to FIGS. 49-51, alternate embodiments of frame 200 are shown and described. Preferably, frames 200 of FIGS. 49-51 are partially, substantially or completely collapsible. Accordingly, the overall height of frame 200 can be reduced for insertion of frame 200 between end plates $E_1$, $E_2$ and the space between end plates $E_1$, $E_2$ does not have to be enlarged to the final and/or desired dimensions in order to accommodate frame 200 when in its partially or fully expanded condition. Frame 200 can be compressed in such a manner so as to bow arcuately outward (FIG. 49) or in an accordion-like manner (FIG. 50). Subsequently, upon the filling space "S" with settable material 110, end plates $E_1$, $E_2$ are forced apart and frame 200 is urged to take on its uncollapsed configuration. In the collapsed state, frame 200 would be rigidly secured to at least one of end plates $E_1$, $E_2$. Accordingly, following introduction of settable material 110 into space "S" the leakage of settable material 110 from between end plates $E_1$, $E_2$ and frame 200 is at least substantially reduced and/or stopped.

Figure 52:
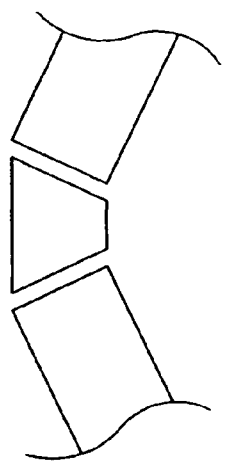
FIG. 52 is an anterior/posterior elevation view of a series of vertebral discs exhibiting a degree of curvature.
Figure 53:
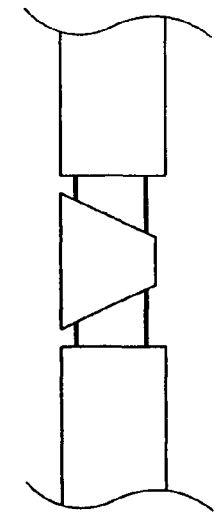
FIG. 53 is an anterior/posterior elevation view of the series of vertebral discs of FIG. 52 following placement of frames between each pair of adjacent vertebral discs.

Turning now to FIGS. 52 and 53, frame(s) 200 can be shaped to correct for anterior/posterior spinal deformities, e.g., scoliosis. For example, in the case of a patient with scoliosis, frame(s) 200 can be wedge-shaped so that when frame(s) 200 is inserted between adjacent end plates $E_1$, $E_2$, frame(s) 200 is able to reposition the vertebrae to restore the spinal column to its natural and/or desired curvature (FIG. 53).

Figure 54:
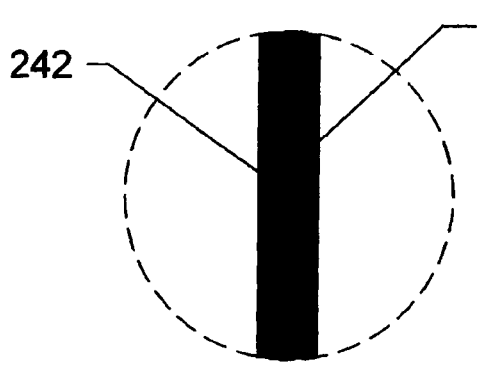
FIG. 54 is an enlarged view of the area indicated 54 of FIG. 17 illustrating an exemplary cross-sectional profile of the wall of the frame.
Figure 55:
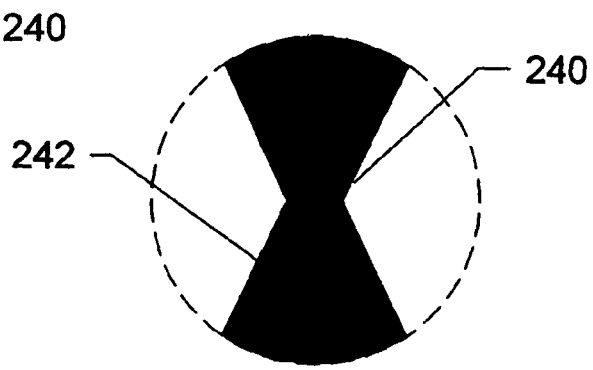
FIG. 55 is an enlarged view of the area indicated 54 of FIG. 17 illustrating another exemplary cross-sectional profile of the wall of the frame.
Figure 56:
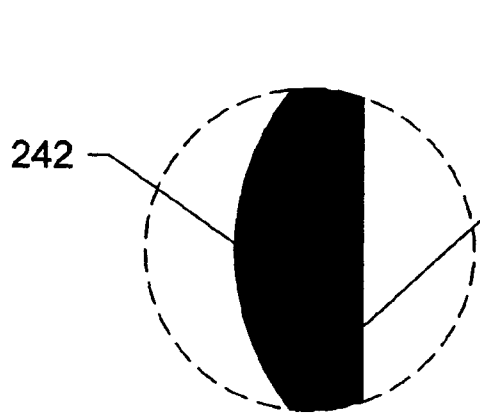
FIG. 56 is an enlarged view of the area indicated 54 of FIG. 17 illustrating yet another exemplary cross-sectional profile of the wall of the frame.
Figure 57:
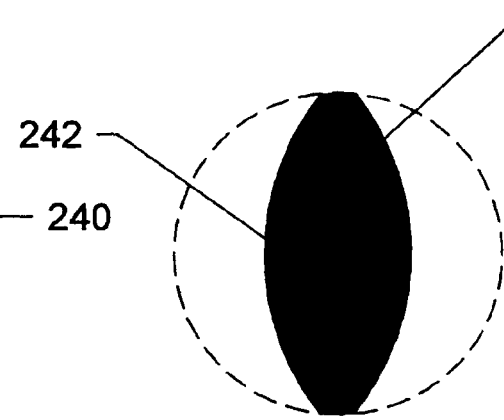
FIG. 57 is an enlarged view of the area indicated 54 of FIG. 17 illustrating still another exemplary cross-sectional profile of the wall of the frame.
Figure 58:
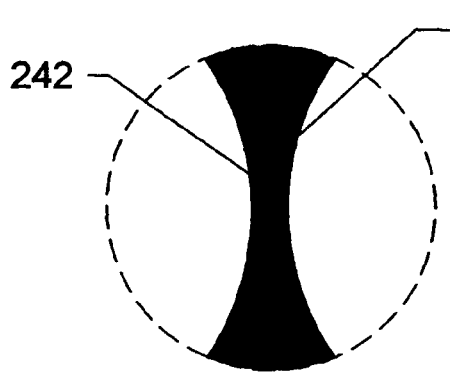
FIG. 58 is an enlarged view of the area indicated 54 of FIG. 17 illustrating a further exemplary cross-sectional profile of the wall of the frame.
Figure 59:
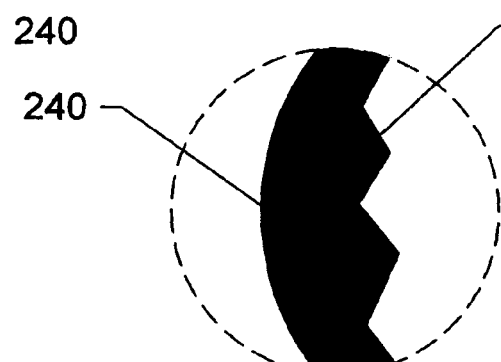
FIG. 59 is an enlarged view of the area indicated 54 of FIG. 17 illustrating an additional exemplary cross-sectional profile of the wall of the frame.

Turning now to FIGS. 54-59, embodiments of the cross-sectional profile of the wall of exemplary frames 200, are shown and described. As seen in FIG. 54, frame 200 can have substantially parallel inner and outer walls 240, 242, respectively. In FIG. 55, it is seen that frame 200 can have a wall which has a substantially hour-glass shaped cross-sectional profile. In FIG. 56, it is seen that frame 200 can include a planar inner wall 240 and an arcuate or convex outer wall 242. Alternatively, as seen in FIG. 57, both inner and outer walls 240, 242 can be convex or, as seen in FIG. 58, both inner and outer walls 240, 242 can be concave. As seen in FIG. 59, frame 200 can include a convex outer wall 240 and a saw-toothed inner wall 242. While various exemplary embodiments have been shown and described, it is envisioned that the various features of the embodiments shown in FIGS. 54-59 can be interchanged with one another without departing from the scope and/or breadth of the present disclosure.

Figure 60:
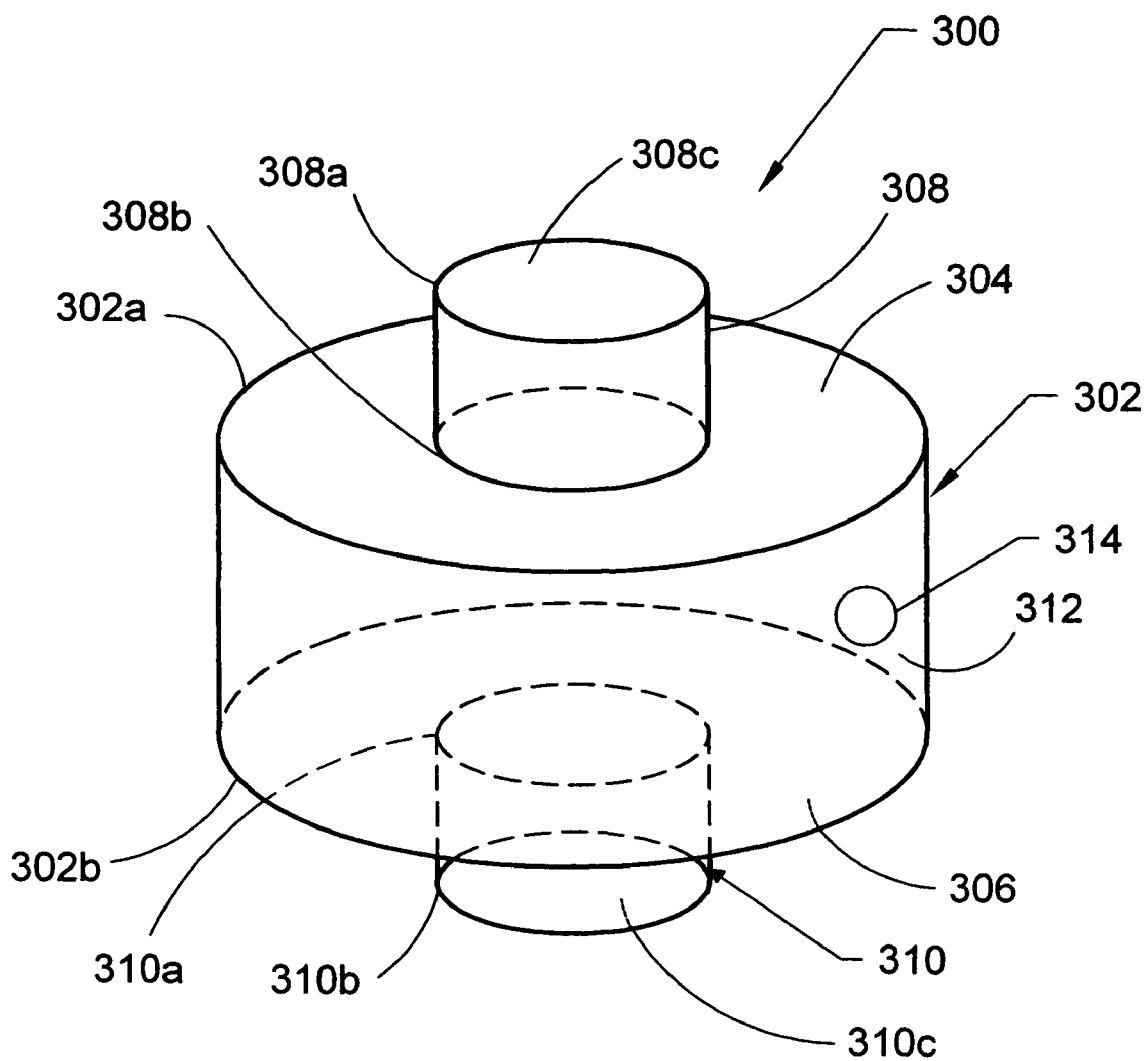
FIG. 60 is a perspective view of frame according to an alternate embodiment of the present disclosure.

Turning now to FIG. 60, a frame in accordance with an alternate embodiment of the present disclosure is generally designated 300. As seen in FIG. 60, frame 300 includes a cylindrical body portion 302 defining an upper surface 304 and a lower surface 306. Frame 300 preferably further includes a first stub 308 extending from upper surface 304 and a second stub 310 extending from lower surface 306. Body portion 302 of frame 300 is defined by an upper ring 302a and a lower ring 302b, first stub 308 is defined by an upper ring 308a and a lower ring 308b, and second stub 310 is defined by an upper ring 310a and a lower ring 310b. Preferably, rings 302a, 302b, 308a, 308b, 310a and 310b are fabricated from a metal wire or the like. Frame 300 further includes a membrane 312 enclosing and operatively connected to rings 302a, 302b, 308a, 308b, 310a and 310b therein in a manner such that when frame 300 is in an expanded condition, body portion 302, first stub 308 and second stub 310 are substantially concentric with one another. Preferably, membrane 312 is fabricated from polymer or a thin metal fabric/weave. Alternatively, other biocompatible materials may be used to fabricate membrane 312. In order for fusion to occur, ends 308c, 310c of stubs 308, 310, respectively, are preferably open to allow settable material 110 to directly contact end plates $E_1$, $E_2$.

In use, frame 300 is preferably inserted between adjacent end plates $E_1$, $E_2$ while in a collapsed condition, e.g., flattened. Subsequently, settable material 110 can be injected into frame 300 through an aperture 314 formed therein. Accordingly, as frame 300 is filled with settable material 110, frame 300 begins to expand and take shape. In an embodiment, it is envisioned that frame 300 may have a pre-defined shape, wherein, as frame 300 is filled with settable material 110, frame 300 assumes its pre-defined shape. In addition, as frame 300 begins to expand between adjacent end plates $E_1$, $E_2$, frame begins to press against end plates $E_1$, $E_2$ and urge end plates $E_1$, $E_2$ apart.

Figure 61:
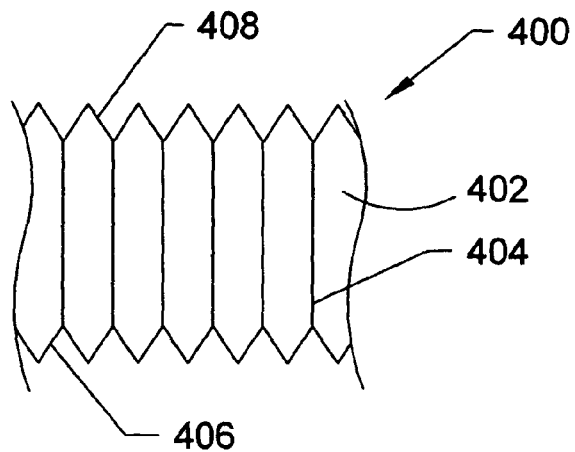
FIG. 61 is a side elevational view of a portion of a frame constructed in accordance with another embodiment of the present disclosure.
Figure 62:
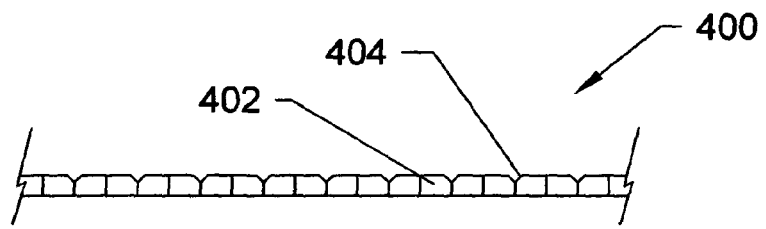
FIG. 62 is a top plan view of the portion of the frame of FIG. 61 shown in a planar configuration.
Figure 63:
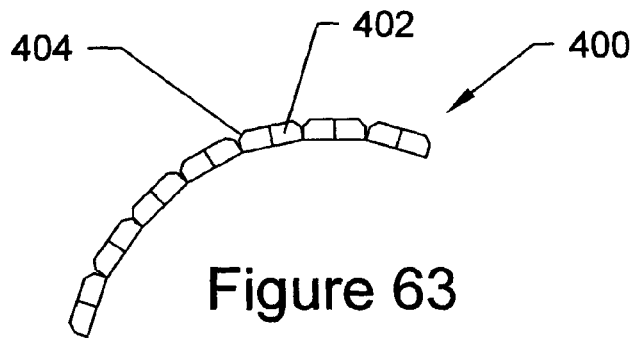
FIG. 63 is a top plan view of the portion of the frame of FIG. 61 shown in an arcuate configuration.

Turning now to FIGS. 61-63, a portion of a frame in accordance with an alternate embodiment of the present disclosure is shown as 400. Frame 400 is flexible and is defined by a plurality of segments 402, each hingedly connected to one another, such as, for example, by a living hinge 404. As such, frame 400 can be bent, as desired, from a linear configuration, as seen in FIG. 62, to any number of arcuate configurations, as seen in FIG. 63. Each segment 402 of frame 400 can include an upper 408 and/or a lower 406 spike, respectively. The length/circumference of this type of frame could be customized by cutting off unneeded segments.

Figure 64:
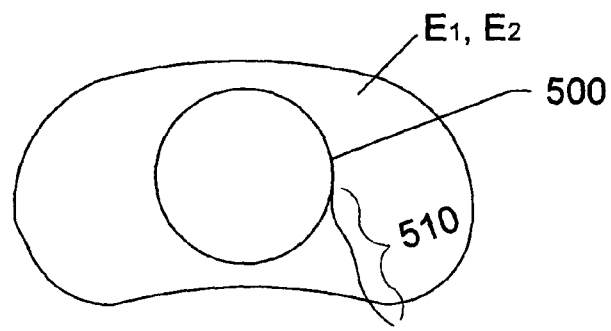
FIG. 64 is a top plan view of a vertebral disc of FIG. 1 illustrating a stage in the insertion of a frame between the adjacent vertebral discs of FIG. 1.
Figure 65:
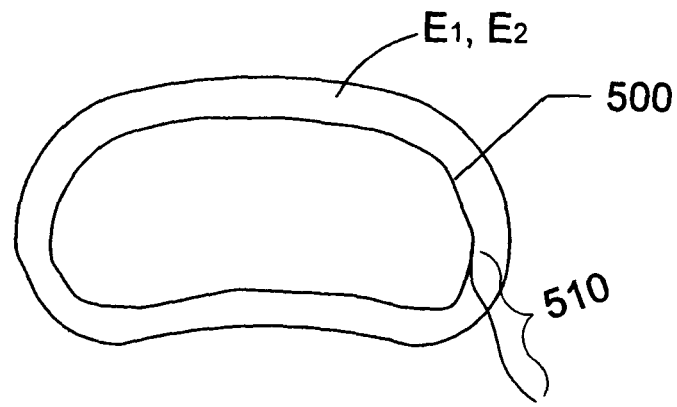
FIG. 65 is a top plan view of a vertebral disc of FIG. 64 illustrating another stage in the insertion of the frame of FIG. 64 between the vertebral discs of FIG. 1.
Figure 66:
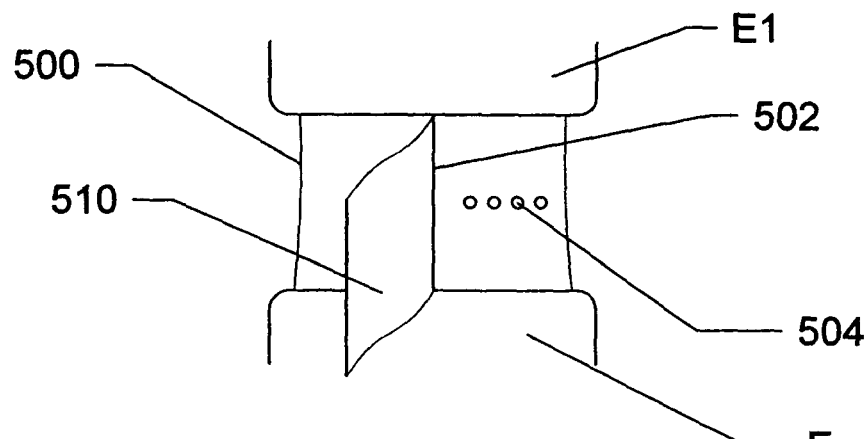
FIG. 66 is a side elevational view illustrating the positioning of the frame of FIGS. 64 and 65 between the vertebral discs of FIG. 1.
Figure 67:
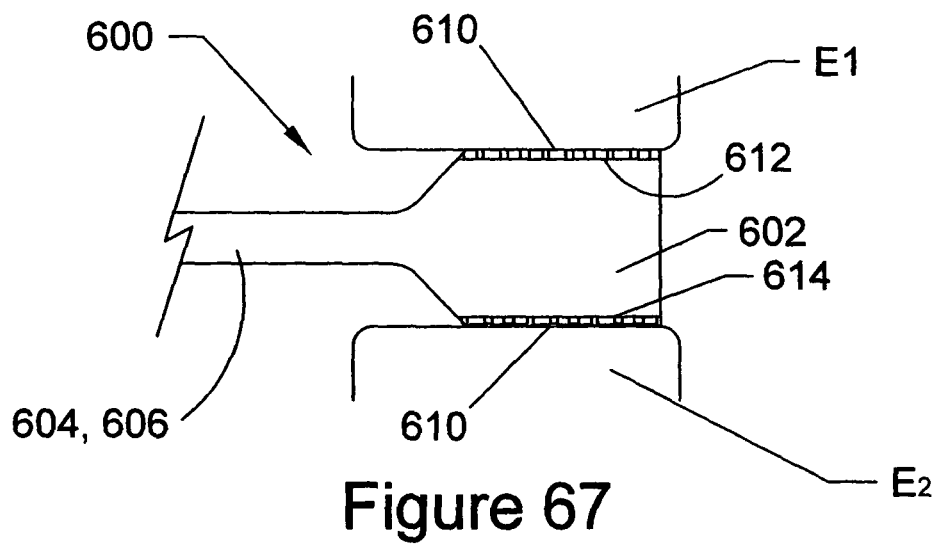
FIG. 67 is a side elevational view of the vertebral discs of FIG. 1 illustrating the positioning of an exemplary frame therebetween.
Figure 68:
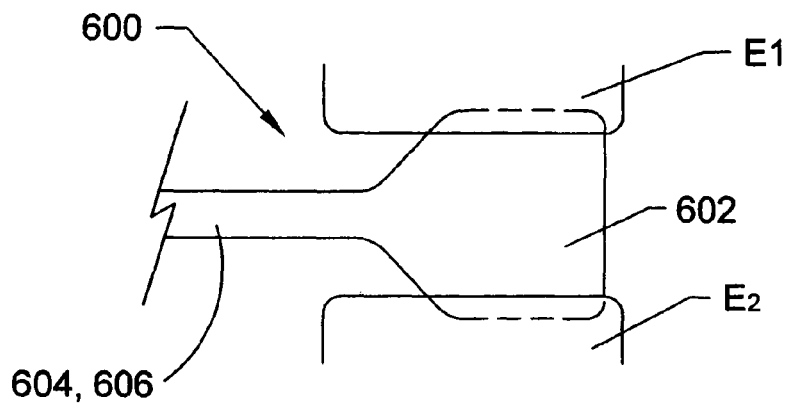
FIG. 68 is a side elevational view of the vertebral discs of FIG. 1 illustrating the positioning of another exemplary frame therebetween.

Turning now to FIGS. 64-66, a flexible frame according to another embodiment of the present disclosure is shown as 500. Frame 500 can be adjusted to accommodate different surgical approaches, disc spaces sizes, etc. In addition, frame 500 can be adjusted as needed and/or desired to define a relatively smaller frame 500, as seen in FIG. 64, or a relatively larger frame 500, as seen in FIG. 65. Accordingly, once frame 500 is inserted between end plates $E_1$, $E_2$, frame 500 can be adjusted as needed. If excess material 510 of frame 500 remains, following placement of frame 500 between end plates $E_1$, $E_2$, the excess material 510 can be either trimmed off, tucked against the remainder of frame 500 and kept in position by a collar or loop 502 on the inside or the outside of frame 500. It is envisioned that frame 500 can include a series of apertures 504 to permit adjustment of frame 500 as needed.

Figure 69:
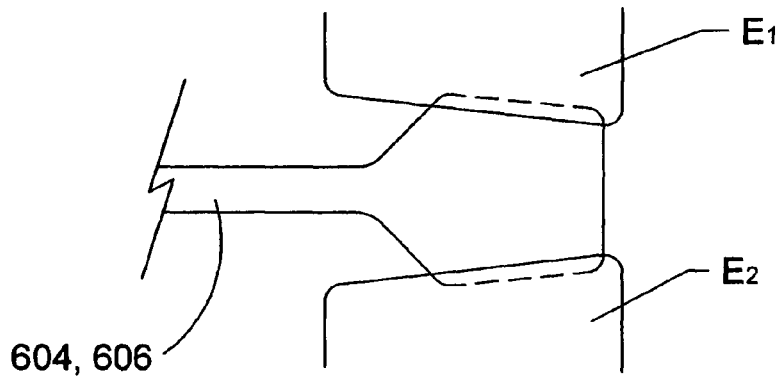
FIG. 69 is a side elevational view of the vertebral discs of FIG. 1 illustrating the positioning of yet another exemplary frame therebetween.
Figure 70:
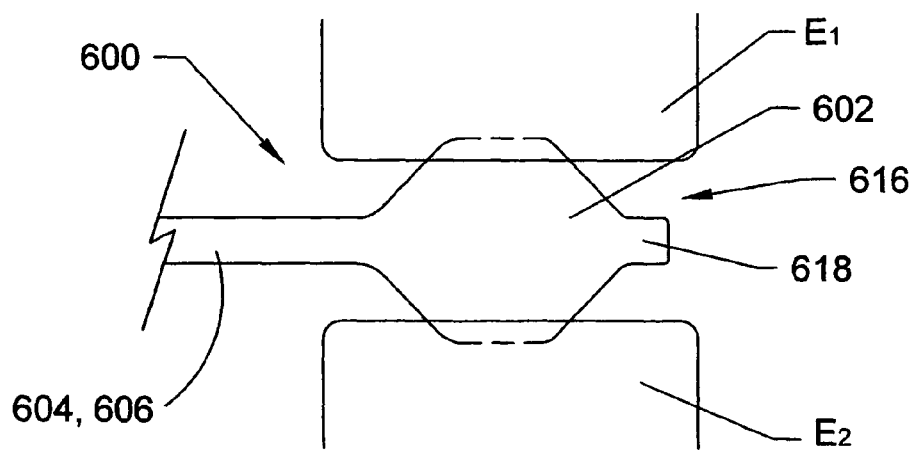
FIG. 70 is a side elevational view of the vertebral discs of FIG. 1 illustrating the positioning of still another exemplary frame therebetween.
Figure 71:
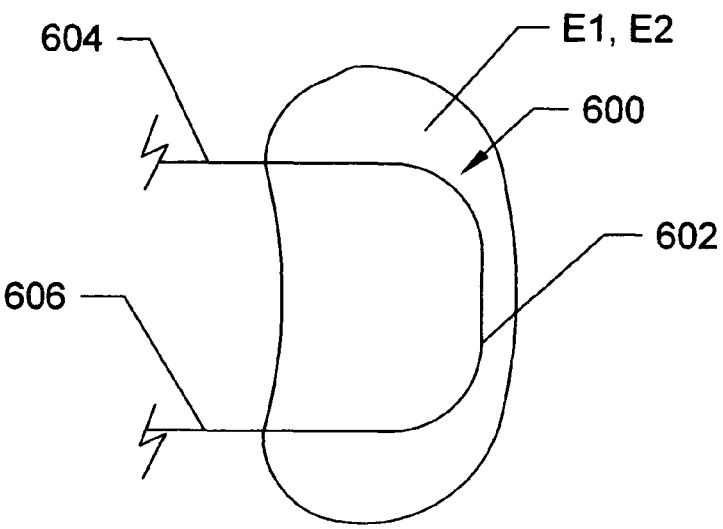
FIG. 71 is a top plan view of vertebral discs of FIGS. 67-70 illustrating the exemplary positioning of the frame therebetween.
Figure 72:
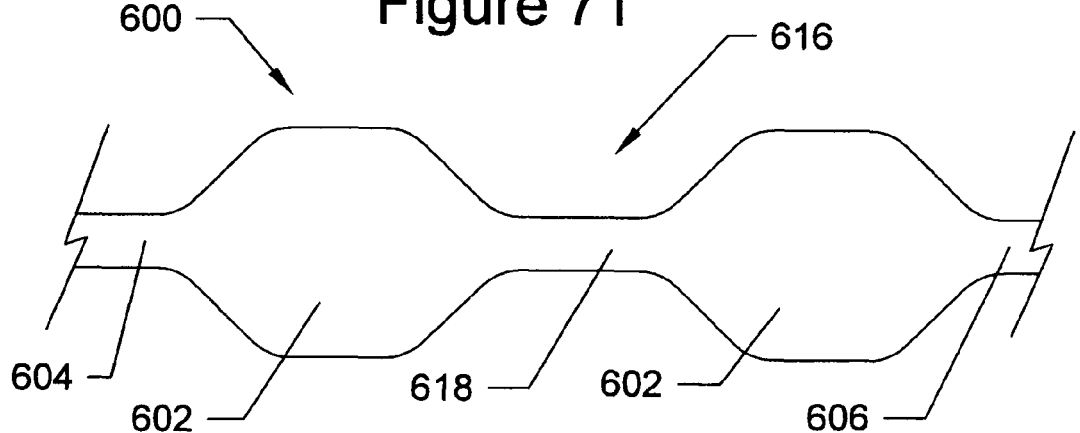
FIG. 72 is a plan view of the frame of FIG. 70 when in an elongated condition.
Figure 73:
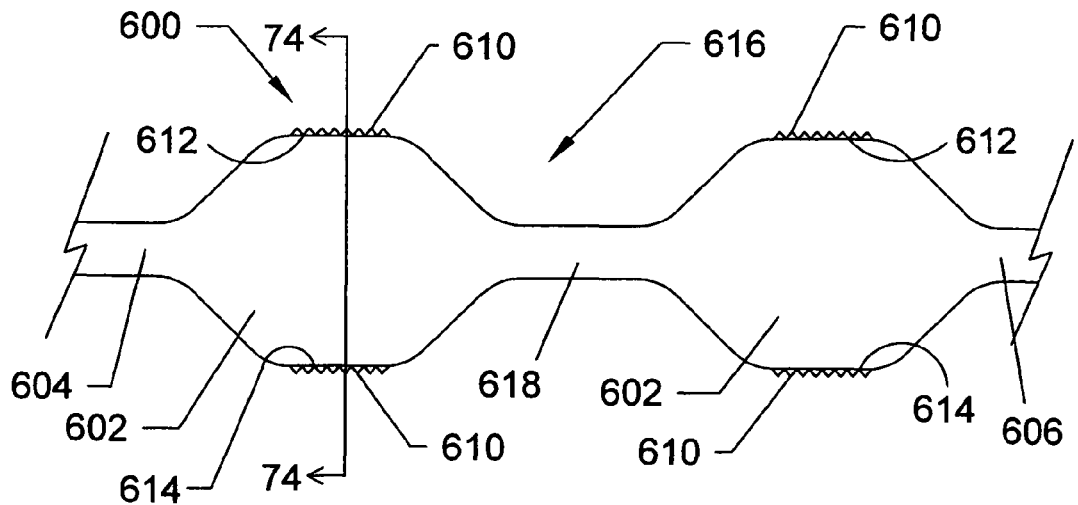
FIG. 73 is a plan view of the frame of FIG. 72 including gripping elements provided thereon.
Figures 74, 75:
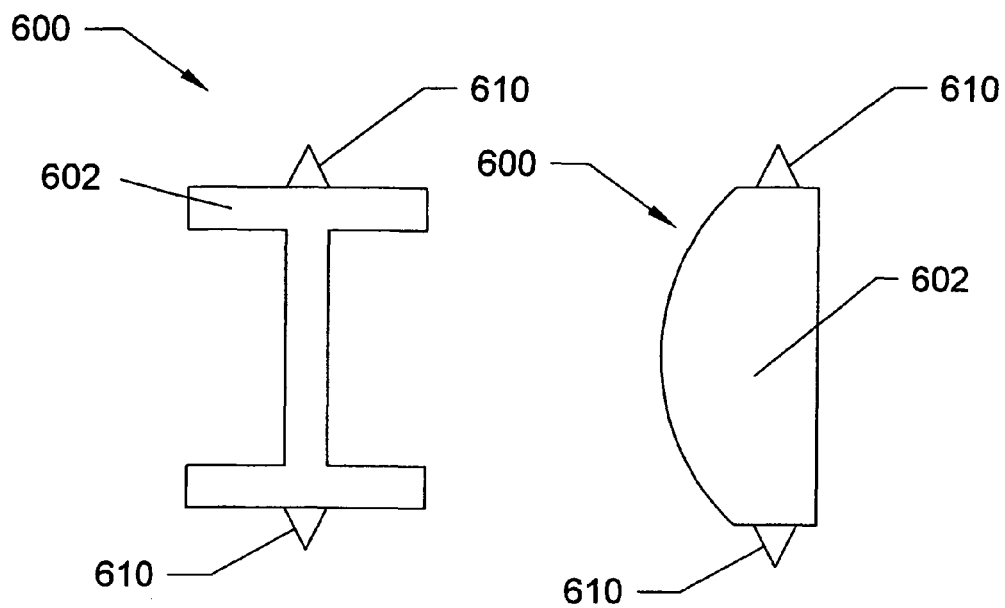
FIG. 74 is a cross-sectional elevational view of the frame of FIG. 73 as taken through section 74-74 of FIG. 73.
FIG. 75 is a cross-sectional elevational view of an alternate embodiment of the frame of FIG. 73 as taken through section 74-74 of FIG. 73.
Figure 76:
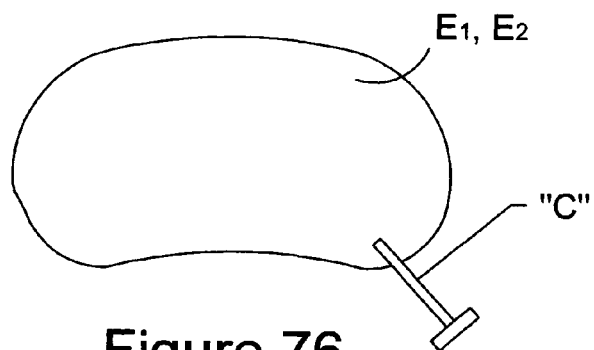
FIG. 76 is a top plan view of a vertebral disc of FIG. 1 illustrating a stage of a method of inserting a frame between the vertebral discs of FIG. 1.
Figure 77:
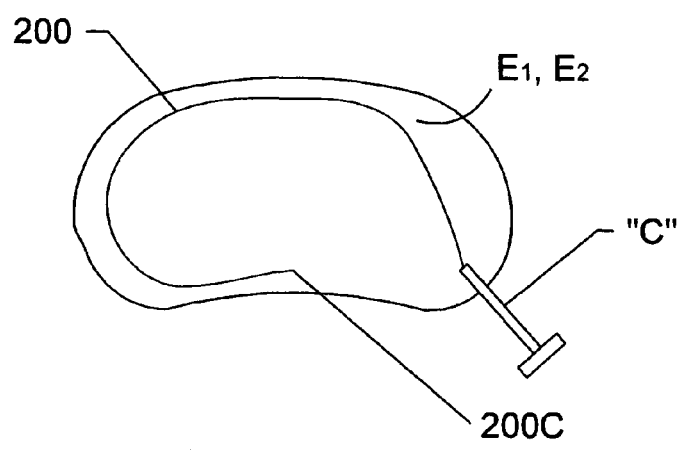
FIG. 77 is a top plan view of the vertebral disc of FIG. 76 illustrating another stage of the method of inserting the frame between the vertebral discs of FIG. 1.
Figure 78:
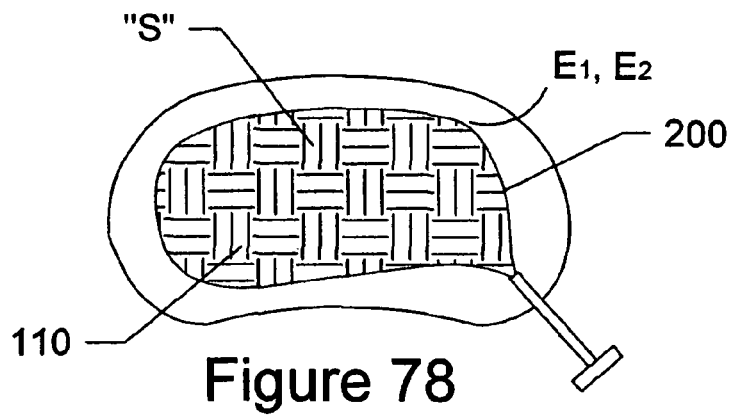
FIG. 78 is a top plan view of the vertebral disc of FIGS. 76 and 77 illustrating yet another stage of the method of inserting the frame between the vertebral discs of FIG. 1.
Figure 79:
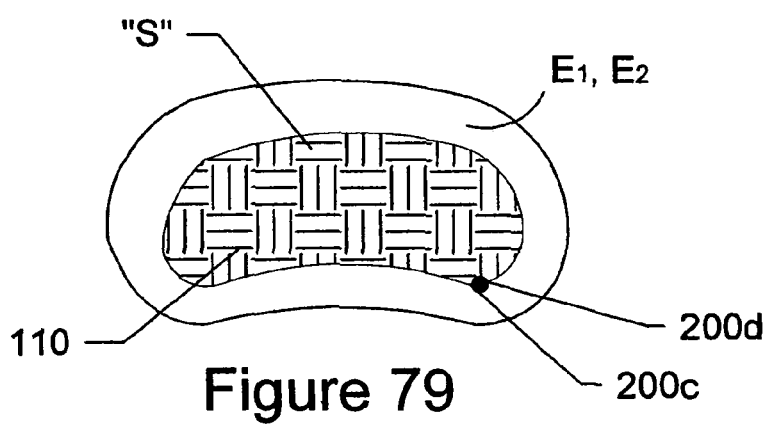
FIG. 79 is a top plan view of the vertebral disc of FIGS. 76-78 illustrating still another stage of the method of inserting the frame between the vertebral discs of FIG. 1.

Turning now to FIGS. 67-75, a ribbon or band-like frame, in accordance with another embodiment of the present disclosure, is shown generally as 600. Frame 600 includes at least a flexible body portion 602 and a first and a second tail 604, 606, respectively, extending therefrom. Body portion 602 can be shaped as desired and/or needed to accommodate the shape of end plates $E_1$, $E_2$. Preferably, tails 604, 606 extend from opposite ends of body portion 602. In this manner, when body portion 602 is inserted into position between end plates $E_1$, $E_2$, such that body portion 602 substantially approximates the curvature of end plates $E_1$, $E_2$ (FIG. 71), tails 604 and 606 extend from end plates $E_1$, $E_2$ in a substantially parallel manner (FIGS. 67-70). As seen in FIGS. 67 and 73-75, body portion 602 can include a series of spikes or ridges 610 formed along at least one of an upper edge 612 and a lower edge 614, thereof. Upper and lower edges 612, 614 of body portion 602 can be substantially parallel to one another (FIG. 68) or, alternatively, upper and lower edges 612, 614 can be shaped to create a body portion 602 having a wedge shape when inserted between end plates $E_1$, $E_2$ (FIG. 69). As seen in FIGS. 70-73, body portion can include a region of reduced thickness 616, wherein frame 600 includes a distal end 618 having a reduced thickness as compared to the remainder of body portion 602. As seen in FIGS. 74 and 75, body portion 602 can have a cross-section which is in the shape of an "I-beam" (FIG. 74) or have an arcuate inner and/or outer wall (FIG. 75).

Turning now to FIGS. 76-85, various methods and/or surgical techniques of inserting the frames of the present disclosure, between adjacent end plates $E_1$, $E_2$ of vertebral discs and the instruments for accomplishing such methods will be shown and described. Generally, the surgical technique includes the steps of: 1) accessing the disc space (Step 1); 2) removing the desired and/or necessary disc material from the disc space (Step 2); 3) distracting the disc space using paddle distractors, lamina spreaders, pedicle screws and the like (Step 3); and 4) preparing the end plates, using curettes, rasps, chisels and the like, so that the resulting bleeding end plate surfaces have an improved ability to adhere to the settable material both physically and biologically, to enhance fusion processes.

As seen in FIGS. 76-79, according to one method, the distal tip of a cannulated instrument, such as a cannula "C", is inserted between the adjacent end plates $E_1$, $E_2$ (FIG. 76); a ribbon or band-like frame, similar to frame 200 of FIGS. 24-26, is introduced into the disc space so as to approximate the geometry of end plates $E_1$, $E_2$ (FIG. 77); distal end 200c of frame 200 is then reintroduced into and through the distal end of cannula "C" so as to define a space "S" (FIG. 78); settable material 110 is then injected, through cannula "C", into space "S" (FIG. 78); and distal end 200c and proximal end 200d of frame 200 are joined to one another, as described above, to close frame 200 and inhibit the escape of settable material therefrom (FIG. 79) from between the side frame and the top and bottom end plates.

Figure 80:
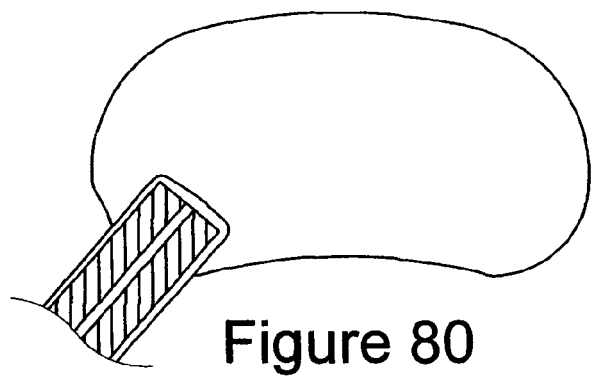
FIG. 80 is a top plan view of a vertebral disc of FIG. 1 illustrating a stage of another method of inserting a frame between the vertebral discs of FIG. 1.
Figure 81:
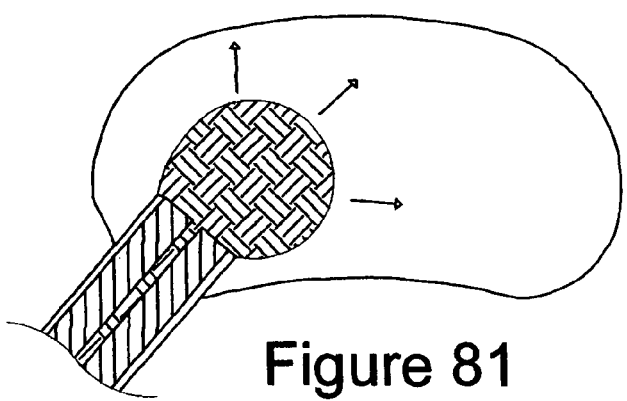
FIG. 81 is a top plan view of the vertebral disc of FIG. 80 illustrating another stage of the method of inserting the frame between the vertebral discs of FIG. 1.

As seen in FIGS. 80 and 81, according to another method, a ribbon or band-like frame similar to frame 600 disclosed above is placed around the distal end of a cannula "C"; the distal end of cannula "C" is inserted between end plates $E_1$, $E_2$ (FIG. 80); and with the distal end of cannula "C" so inserted, settable material 110 is injected, through cannula "C", into space "S" bound by frame 600 and the vertebral end plate. As settable material 110 is injected into space "S", frame 600 is expanded outwardly (as indicated by the arrows of FIG. 81) to fill the area of end plates $E_1$, $E_2$.

Figure 82:
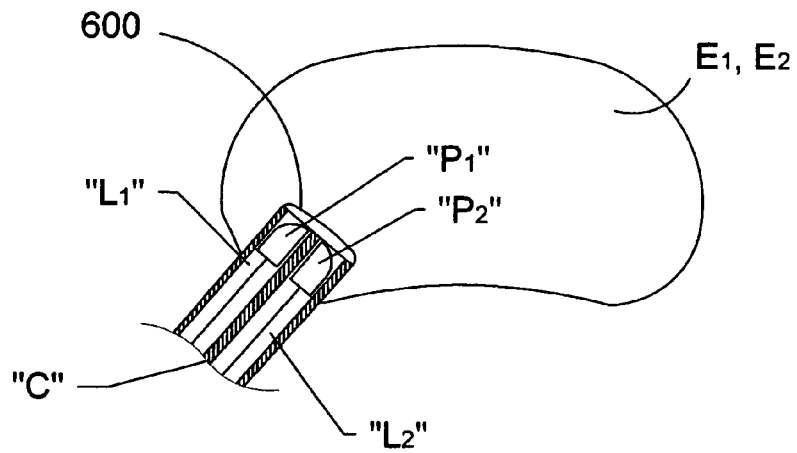
FIG. 82 is a top plan view of a vertebral disc of FIG. 1 illustrating a stage of yet another method of inserting a frame between the vertebral discs of FIG. 1.
Figure 83:
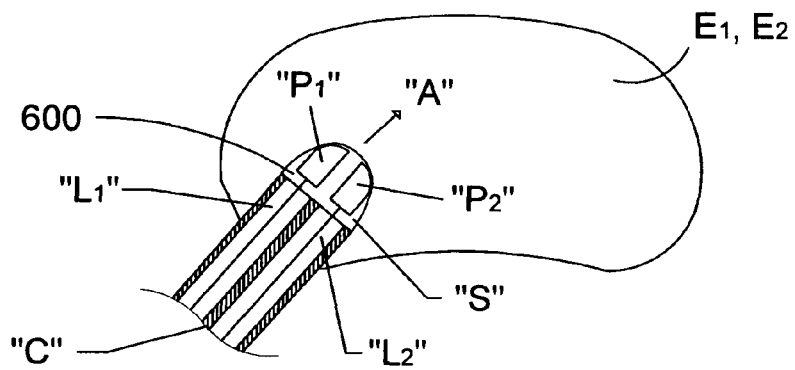
FIG. 83 is a top plan view of the vertebral disc of FIG. 82 illustrating another stage of the method of inserting the frame between the vertebral discs of FIG. 1.
Figure 84:
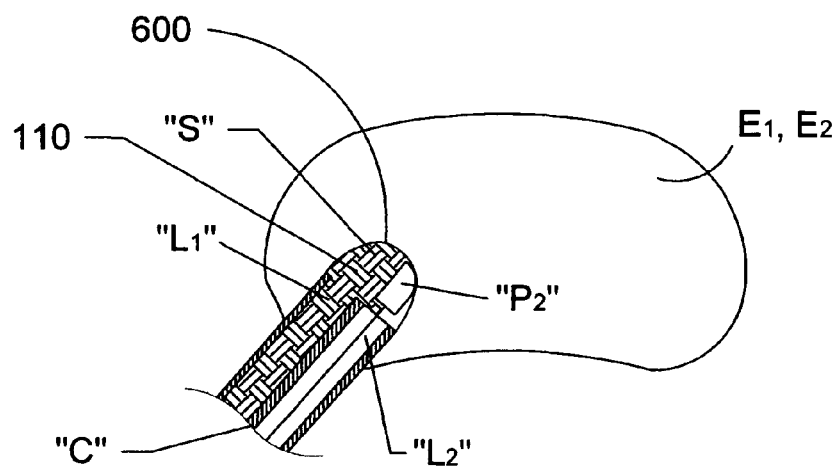
FIG. 84 is a top plan view of the vertebral disc of FIGS. 82 and 83 illustrating yet another stage of the method of inserting the frame between the vertebral discs of FIG. 1.
Figure 85:
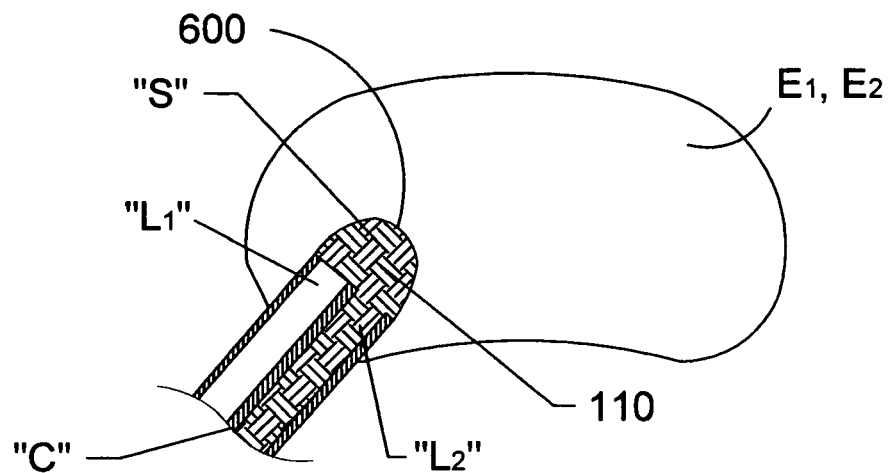
FIG. 85 is a top plan view of the vertebral disc of FIG. 82-84 illustrating still another stage of the method of inserting the frame between the vertebral discs of FIG. 1.

As seen in FIGS. 82-85, according to yet another method, a ribbon or band-like frame similar to frame 600 disclosed above is placed around the distal end of a cannula "C" having double lumens $L_1$, $L_2$ with each lumen $L_1$, $L_2$ including a plunger or driver $P_1$, $P_2$, respectively. As seen in FIG. 82, the distal end of cannula "C" is inserted between end plates $E_1$, $E_2$. With the distal end of cannula "C" so positioned, as seen in FIG. 83, at least one plunger $P_1$, $P_2$ is advanced in the direction of arrow "A" to expand frame 600 across end plates $E_1$, $E_2$. As seen in FIG. 84, at least one plunger $P_1$, $P_2$ can be withdrawn from lumen $L_1$, $L_2$ and settable material 110 injected into space "S" through the empty one of lumens $L_1$, $L_2$. As seen in FIG. 85, to completely fill space "S" with settable material 110, the other of plungers $P_1$, $P_2$ is withdrawn from lumen $L_1$, $L_2$ so that settable material 110 can be injected therethrough. It is envisioned that more than two plungers $P_1$, $P_2$ can be provided. Moreover, plungers $P_1$, $P_2$ can have different shapes and/or sizes, and can be strategically deployed to customize the shape and location of frame 600.

In any of the methods described above, once the frame has been filled with the desired amount of settable material 110, cannula "C" is removed and the frame can be closed in any of the manners disclosed above. Alternatively, the frame can be removed from between end plates $E_1$, $E_2$ once sufficient time has passed to allow settable material 110 to set.

It is envisioned that multiple frames can be deployed from a single cannula "C" to provide multiple frames between end plates $E_1$, $E_2$. In addition, it is envisioned that the multiple frames can be concentric with one another, wherein the settable material injected in the "outer" frame has different characteristics than the settable material injected into the "inner" frame. For example, the settable material in the "outer" frame as compared to the "inner" frame may be harder, softer, denser, have a different porosity, be more or less osteoinductive or osteoconductive, or have any combination of these characteristics to customize the most enhanced fusion process.

Figure 86:
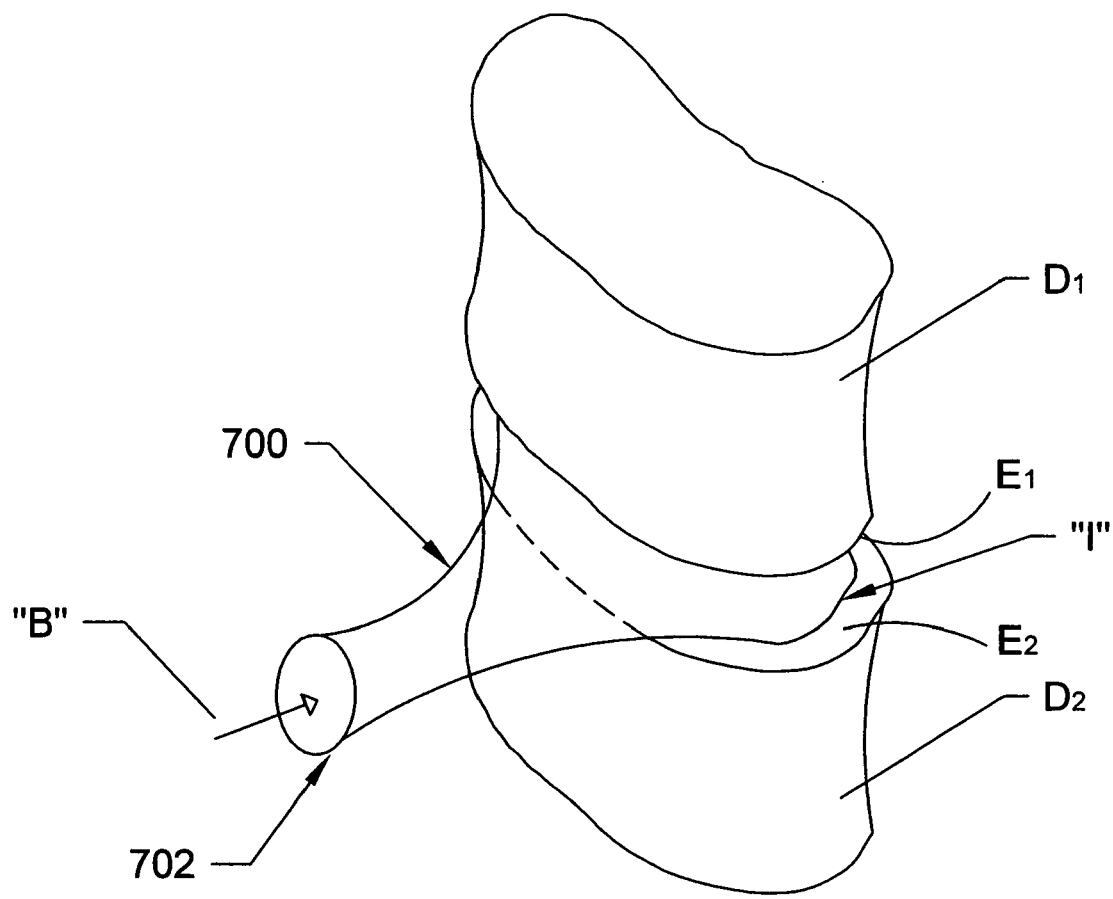
FIG. 86 is a perspective view of the vertebral discs of FIG. 1 illustrating a method of injecting settable material between the adjacent vertebral discs.

Turning now to FIG. 86, an alternative method of introducing settable material 110 between end plates $E_1$, $E_2$ of adjacent vertebral discs $D_1$, $D_2$, is shown and described. As seen in FIG. 86, a frame 700, in the form of a biodegradable/resorbable sac or balloon is provided. Frame 700 is inserted into the intervertebral space "I" such that frame 700 at least partially fills intervertebral space "I". Once frame 700 is in the desired position between end plates $E_1$, $E_2$, settable material (not shown) is injected into frame 700, through an opening 702 formed therein, in the direction of arrow "B" to thereby fill frame 700 and distract vertebral discs $D_1$, $D_2$.

Preferably, frame 700 is fabricated from a degradable, and/or resorbable material so that fusion across the end plate will occur. More preferably, the top and the bottom portions of frame 700 (i.e., the portions of frame 700 in contact with end plates $E_1$, $E_2$) are fabricated from a material which can/will degrade more quickly than the remainder of frame 700. In this manner, fusion between the settable material and end plates $E_1$, $E_2$ can proceed more quickly.

Turning now to FIGS. 87-89, exemplary templates, for forming any of the frames disclosed above, are shown. For example, templates 750 can be rectangular (FIG. 87) or templates 752 can be triangular (FIG. 88). Additionally, templates 750, 752 can be provided with a handle 754 (FIGS. 87 and 88) or template 756 can be provided without a handle (FIG. 89).

Turning now to FIGS. 90-92, a flexible frame, according to yet another embodiment of the present disclosure, is shown as 800. Preferably, frame 800 is fabricated from a straw-like material that is flexible enough to be contoured into a variety of shapes to accommodate various patient specific needs. For example, as seen in FIG. 91, frame 800 can be shaped in a wave-like configuration or, as seen in FIG. 92, frame 800 can be shaped in a spiral configuration. Various other configurations are contemplated and within the scope of the present disclosure. Preferably, straw-like frame 800 can be made from strands of resorbable polymers that would allow the material to be fused to end plates $E_1$, $E_2$. It is envisioned that frame 800 can include a flexible perimetral wall 801 which together with end plates $E_1$, $E_2$ will bound and/or encase settable material 110 therein. In this manner, settable material 110 will fuse with the prepared end plates.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An intervertebral implant system for intervertebral implantation, comprising:
    A first ribbon-like or band-like frame having a first peripheral wall defining a first space therein, a second ribbon-like or band-like frame having a second peripheral wall defining a second space therein; and
    first and a second settable materials that are introduced into the first and second spaces, respectively of the first and second ribbon-like or band like frames,
    wherein the first ribbon-like or band-like frame includes a pair of free ends joinable to one another, or at least one opening in the first peripheral wall, and the second ribbon-like or band-like frame includes a pair of free ends joinable to one another, or at least one opening in the second peripheral wall, and the first and second materials include at least one of bone, composites, polymers of bone growth material, collagen, and insoluble collagen derivatives; and wherein the first and second settable materials each have an initial fluid condition and are cured to a hardened condition in the first and second spaces respectively, wherein the settable material in the first space is harder and has a different porosity than the settable material in the second space.

2. The intervertebral implant system of claim 1, wherein each frame is constructed from at least one of titanium, titanium alloy, steel, shape memory alloy, resorbable polymer, non-resorbable polymer, ceramic, and organic materials.

3. The intervertebral implant system of claim 2, wherein the first and second settable materials are biocompatible load bearing materials.

4. The intervertebral implant system of claim 3, wherein the first and second settable materials are injectable into the first and second spaces defined by each frame.

5. The intervertebral implant system of claim 1, wherein at least one of an upper edge and a lower edge of each frame is shaped.

6. The intervertebral implant system of claim 1, wherein at least one of the upper edge of each frame and the lower edge of each frame includes at least one of a plurality of projections formed along a length of each frame, and a continuous projection extending along a length of each frame.

7. The intervertebral implant system of claim 1, wherein each frame is flexible along at least a portion of a length thereof.

8. The intervertebral implant system of claim 1, further comprising a cap positionable within the space defined by each frame, the cap being dimensioned to extend beyond at least each free end of each frame.

9. The intervertebral implant system of claim 1, wherein each frame is linearly expandable.

10. The intervertebral implant system of claim 1, further comprising at least one plug configured and dimensioned for insertion into each opening of each frame, wherein the at least one plug prevents the escape of the first and second settable materials from the first and second spaces.

11. The intervertebral implant system of claim 1, wherein the peripheral wall of each frame is at least partially collapsible.

12. The intervertebral implant system of claim 1, wherein each frame is substantially wedge-shaped.

13. The intervertebral implant system of claim 1, wherein the first or second peripheral wall includes at least one of a planar inner surface and a planar outer surface.

14. The intervertebral implant system of claim 1, wherein the first or second peripheral wall includes at least one of a convex inner surface and a planar outer surface.

15. The intervertebral implant system of claim 1, wherein the first or second peripheral wall includes at least one of a concave inner surface and a planar outer surface.

16. The intervertebral implant system of claim 1, wherein the first or second peripheral wall includes at least one of a saw-toothed inner and outer surface.

17. The intervertebral implant system of claim 1, wherein a length of the perimetral wall defining the first and second space of each frame is adjustable.

18. The intervertebral implant system of claim 1, wherein the first or second peripheral wall has an I-shaped transverse cross-sectional profile.

19. The intervertebral implant system of claim 1, wherein the first or second peripheral wall is fabricated from strands of resorbable polymers.

20. The intervertebral implant system of claim 1, further comprising:
   a support plate securable to adjacent intervertebral discs; and
   a fixation means extendable through the support plate and into the first or second peripheral wall of the frame.

21. The intervertebral implant system of claim 1, wherein the first frame and the second frame are concentric with each other.

* * * * *